(12) United States Patent
Olson et al.

(10) Patent No.: US 11,672,437 B2
(45) Date of Patent: Jun. 13, 2023

(54) METHOD AND DEVICE FOR TISSUE MONITORING AND HEART RATE DETECTION

(71) Applicant: HAPPY HEALTH, INC., Austin, TX (US)

(72) Inventors: Byron Olson, Boone, IA (US); Paulo E. Xavier Da Silveira, Boulder, CO (US); Nithin O. Rajan, Austin, TX (US); Dustin M. Freckleton, Austin, TX (US)

(73) Assignee: Happy Health, Inc., Austin, TX (US)

( * ) Notice: Subject to any disclaimer, the term of this patent is extended or adjusted under 35 U.S.C. 154(b) by 297 days.

(21) Appl. No.: 16/171,022

(22) PCT Filed: Apr. 25, 2017

(86) PCT No.: PCT/US2017/029467
§ 371 (c)(1),
(2) Date: Oct. 25, 2018

(87) PCT Pub. No.: WO2017/189612
PCT Pub. Date: Nov. 2, 2017

(65) Prior Publication Data
US 2019/0133471 A1 May 9, 2019

Related U.S. Application Data

(60) Provisional application No. 62/327,235, filed on Apr. 25, 2016.

(51) Int. Cl.
*A61B 5/024* (2006.01)
*A61B 5/0245* (2006.01)
(Continued)

(52) U.S. Cl.
CPC ........ *A61B 5/02438* (2013.01); *A61B 5/0245* (2013.01); *A61B 5/11* (2013.01);
(Continued)

(58) Field of Classification Search
CPC .............. A61B 5/02438; A61B 5/0245; A61B 5/02416; A61B 5/11; A61B 5/14551;
(Continued)

(56) References Cited

U.S. PATENT DOCUMENTS 9,717,427 B2 * 8/2017 Kelner ................... A61B 5/725
10,426,360 B2 * 10/2019 Nousiainen .......... A61B 5/7203
(Continued)

FOREIGN PATENT DOCUMENTS

WO  WO/2017/189612  11/2017

OTHER PUBLICATIONS

International Search Report and Written Opinion for corresponding PCT Application No. PCT/US2017/029467 dated Nov. 2, 2017.
(Continued)

*Primary Examiner* — Devin B Henson
(74) *Attorney, Agent, or Firm* — Polsinelli PC

(57) ABSTRACT

Provided herein are methods and devices configured to detect the heart rate of a user. The method includes receiving at least one input signal, separating the input signal into signal components, receiving a motion signal from the user, and applying a Bayesian filter to the signal components and the motion signal to estimate the heart rate of the user. The method further includes calculating a combination of at least two reflected light signals from at least two different wavelengths. The device includes a photodetector configured to detect at least one reflected light signal resulting from the emitted at least two different wavelengths and a motion detector for detecting a motion signal. The device also includes a processing component configured to calculate a
(Continued)

combination of the reflected light signals, separate the combination of detected light signals into signal components, and apply a Bayesian filter to the signals.

19 Claims, 19 Drawing Sheets

(51) Int. Cl.
    *A61B 5/11*     (2006.01)
    *A61B 5/00*     (2006.01)
    *A61B 5/1455*     (2006.01)

(52) U.S. Cl.
    CPC .......... *A61B 5/14551* (2013.01); *A61B 5/721* (2013.01); *A61B 5/02416* (2013.01); *A61B 2503/10* (2013.01)

(58) Field of Classification Search
    CPC ....... A61B 5/721; A61B 5/7246; A61B 5/725; A61B 2503/10
    See application file for complete search history.

(56) References Cited

U.S. PATENT DOCUMENTS

| | | | |
|---|---|---|---|
| 10,568,525 B1* | 2/2020 | Wu | A61B 5/0205 |
| 2013/0303922 A1* | 11/2013 | Buchheim | A61B 5/02438 |
| | | | 600/479 |
| 2014/0235965 A1 | 8/2014 | Tran | |
| 2015/0100141 A1 | 4/2015 | Hughes | |
| 2015/0265161 A1 | 9/2015 | Hernandez et al. | |
| 2015/0265217 A1 | 9/2015 | Penders et al. | |
| 2015/0351699 A1 | 12/2015 | Addison et al. | |
| 2017/0258405 A1* | 9/2017 | Sato | A61B 5/7257 |
| 2017/0281027 A1* | 10/2017 | Altmejd | A61B 5/14552 |

OTHER PUBLICATIONS

International Preliminary Report issued in International Application No. PCTUS2017029467, dated Nov. 8, 2018, 12 pages.

* cited by examiner

METHOD AND DEVICE FOR TISSUE MONITORING AND HEART RATE DETECTION

CROSS REFERENCE TO RELATED APPLICATIONS

This application is U.S. National Stage Entry of PCT Application No. PCT/US2017/029467, filed Apr. 25, 2017, which claims priority to U.S. Provisional Application No. 62/327,235, filed Apr. 25, 2016, the contents of each are entirely incorporated by reference herein.

FIELD

The present disclosure generally relates to a method and device for non-invasive tissue monitoring. More particularly, the disclosure relates to an apparatus and method for real-time assessment of heart rate using optical techniques.

BACKGROUND

Monitoring exertion via a heart rate monitor has long been a centerpiece of training for professional and performance athletes, as well as amateurs and retired players. Heart rate monitoring can take the form of the athlete holding one or more fingers on his or her neck and timing the beats per minute with a watch, clock, or stop watch. Additionally, there are sensors that can be worn on the chest. There are other sensors that can be placed on exercise equipment that require the athlete to hold those sensors while measurements are taken.

BRIEF DESCRIPTION OF THE DRAWINGS

So that the manner in which the above recited features of the present disclosure can be understood in detail, a more particular description of the disclosure, may be had by reference to examples, some of which are illustrated in the appended drawings. It is to be noted, however, that the appended drawings illustrate only typical examples of this disclosure, and are therefore not to be considered limiting of its scope, for the disclosure may admit to other equally effective examples.

DETAILED DESCRIPTION

Figure 1:
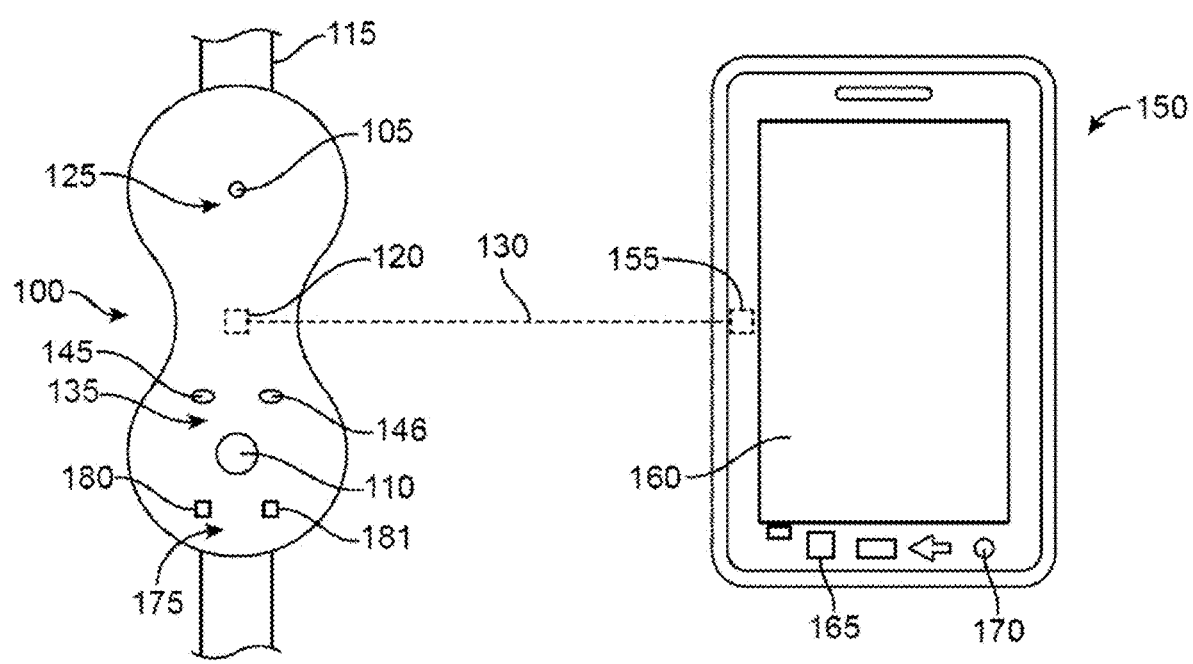
FIG. 1 is a schematic diagram of a non-invasive tissue monitoring device according to an example of the present disclosure.

Various examples of the disclosure are discussed in detail below. While specific implementations are discussed, it should be understood that this is done for illustration purposes only. A person skilled in the relevant art will understand that other components and configurations can be used without parting from the spirit and scope of the disclosure.

It should be understood at the outset that although illustrative implementations of one or more examples are illustrated below, the disclosed device can be implemented using any number of techniques. The disclosure should in no way be limited to the illustrative implementations, drawings, and techniques illustrated herein, but can be modified within the scope of the appended claims along with their full scope of equivalents.

Unless otherwise specified, any use of any form of the terms "connect," "engage," "couple," "attach," or any other term describing an interaction between elements is not meant to limit the interaction to direct interaction between the elements and can also include indirect interaction between the elements described. In the following discussion and in the claims, the terms "including" and "comprising" are used in an open-ended fashion, and thus should be interpreted to mean "including, but not limited to."

The present disclosure generally relates to a method and device for non-invasive tissue monitoring. In at least one example, a method to determine the user's heart rate is provided. The method includes receiving at least one input signal from at least one sensor, receiving a motion signal from a gyroscope or accelerometer, and filtering the input signal and motion signal to estimate a biological indicator of the user. In one example, the input signal is indicative of heart rate and the biological indicator of the user is the user's heart rate. The method can further include separating the at least one input signal into signal components and the filter can be applied to the signal components and the motion signal. The input signal can be derived from an optical signal, a combined optical signal, signal components, or an EKG signal. The input signal will contain information about the heart rate and/or other biological information.

The method can further include repeating the steps above after a period of time and updating the estimate of the heart rate of the user. An expected change in the heart rate can be determined using the motion signal. In at least one example, the estimated heart rate can be updated based on the expected change in heart rate, such as the expected change in heart rate is increasing, decreasing, or unchanging based on a change in motion by the user.

In an example, the input signal can be an optical signal detected by emitting light to the tissue from at least one emitter at at least one wavelength and receiving at least one reflected light signal from the tissue. In one example, the emitter can emit light having at least two wavelengths or at least two emitters can emit light having the same or different wavelengths and the input signal can be a combination of at least two detected light signals. The emitter may include at least one light emitting diode (LEDs), each emitting at a wavelength. In an example, the emitter can include at least two LEDs and the at least two wavelengths of the LEDs can be the same or distinct. In at least one example, at least two emitters can have different spatial locations and the same wavelength. In this example, two LEDs can be physically distinct but have the same center wavelength.

In various examples, the at least two wavelengths are within a range of about 450 nm to about 1100 nm, about 450 nm to about 660 nm, and about 550 nm to about 950 nm. In some examples, at least three wavelengths are emitted and at least three reflected light signals are detected. Non-limiting examples of emitted wavelengths include, but are not limited to 505 nm, 470 nm, 630 nm, 550 nm, 650 nm, 950 nm, 1100 nm, and combinations thereof. In at least one example, 505 nm may be preferred over 640 nm which may be preferred over 470 nm. In the second example, 550 nm may be preferred over 950 nm which may be preferred over 650 nm. While these wavelengths are provided, the present disclosure includes wavelengths within one or more of the above ranges.

The signal can also contain noise, which can come from ambient light, motion, or other sources. Some noise sources (for example, motion and blood volume variation) generate coherent noise that can be subtracted from the signal. Coherent noise refers to noise that is consistent so that it can be removed at each relevant portion. Therefore, the method contemplates processing of the optical signals, and the method further includes calculating a combination of detected reflected light signals. As used herein, a combination refers to a result of combining two or more signals according to a known equation. The known equation can be a simple addition of the signals. In other examples, the equation can be a summation equation that includes weighting factors for the individual signals. In yet other examples, the combination can be based on weighting factors and an additional function. In at least one example, the signals can be from different colored lights that are received. The detected signals from the different wavelengths of emitted light can be weighted such that a one of the signals is more valued than the other. The valuing of the detected signal can be based upon the biological indicator that is of interest or it can be independent of the biological indicator. Furthermore, the weighting can be specific to a user. In other examples, the weighting can be based on the user and the biological indicator of interest.

The method can further include receiving a motion signal from the user using a gyroscope or an accelerometer and applying a Bayesian filter to the input signal and motion signal to estimate the heart rate of the user. The input signal can be the combination of two or more reflected light signals. In at least one example, the input signal can be separated into its signal components before applying the Bayesian filter. The separation of signals can be performed to select one or more of the following: oxygenation monitoring, photoplethysmograph detection, heart rate detection, motion detection, total hemoglobin detection, respiration detection, or hydration detection. The separation of signals can be performed using a bank of filters, at least one adaptive filter, or at least one fixed filter. The Bayesian filter is at least one example of one of the adaptive filters used for the separation of the combined detected signals in addition to the combination with a motion signal. In at least one example, method can include removing motion artifacts in the filter. In this example, the peaks of the motion signal can assist in determining the true peaks in the input signal.

In one example, the combination of detected light signals can be based upon performing a search of a predetermined number of combinations and selecting the combination that provides for an increased accuracy as compared to a single signal. In another example, the combination of detected light signals can be based upon performing a search of all combinations that are within a selected criteria, for example all integer combinations, and selecting the combination that provides for an increased accuracy relative to the single signal. In yet other examples, the increased accuracy as described above can be in relation to other ones of the combinations. In still other examples, the increased accuracy as described above can be in relation to both the single detected signal and other detected light signals of the combination. In one example, the calculated combination is a linear combination of at least two detected light signals to produce an input signal with better performance as compared to a single optical signal. Better performance occurs when adaptive parameters are set so that the magnitude of an error metric is lower than that obtained when adaptive parameters are set to different values. For example, the error metric can be selected as at least one of 1) the root mean-squared difference, 2) the signal power of the difference, 3) the sum of squares of the difference. The difference can be calculated between the heart rate estimate provided by the combination of signals and a reliable measurement, for example, an electrocardiogram (EKG). In another example, the method can further include separating the input signal into its constituent components. This can be done by forming a vector comprised of the original signals multiplied by their optimized weights. This new vector can be used with the pseudo-inverse projection method to determine the quantity of a chromophore of interest.

The method can further include transmitting an alert to an output device. The method can further include communicating the heart rate to a user. The communication of the heart rate to the user can be done in real-time, which includes within one second of the measurement. In other examples, the heart rate is communicated within one microsecond. The present disclosure may require more than one second to compute the heart rate so that there is a lag between the user's actual heart rate and the heart rate that is communicated. In one example, the lag between the user's actual heart rate and the heart rate that is communicated can be five seconds. In other examples, the heart rate can be computed in less than one second. In other examples, the heart rate can be computed and communicated in real-time.

While physiologists and trainers agree that monitoring heart rate is a crude method and a lagging indicator of conditioning, the present technology provides distinct advantages. The present device can present heart rate along with other biological indicators to provide a more accurate depiction of the athlete's performance.

In at least one example, a non-invasive device for optically measuring heart rate is provided. Examples of non-invasive optical-electronic devices configured to determine levels of biological indicators are described in U.S. Pat. No. 8,996,088 entitled APPARATUS AND METHOD FOR IMPROVING TRAINING THRESHOLD, the entire contents of which are incorporated herein by reference. The non-invasive tissue-monitoring device may be used by itself or in combination with other biosensor devices. The tissue-monitoring device includes an emitter configured to emit at least one wavelength of light to a tissue of the user and a photodetector configured to detect at least one reflected light signal from the tissue. The device further includes a processing component configured to calculate a combination of the detected light signals. The processing component can include at least one processor. In at least one example, the processing component can also include memory. The device can further include a motion detector configured to detect the motion of the user. For example, the motion detector can be a gyroscope or an accelerometer. The processing component can further be configured to combine the combination of detected light signals and the motion signal using a Bayesian filter. In at least one example, the processing component can also separate the combination of the detected light signals into its signal components before applying the Bayesian filter. The processing component can further be configured to repeat the steps above after a period of time and update the estimate of the heart rate of the user. An expected change in the heart rate can be determined using the motion signal. In at least one example, the estimated heart rate can be updated based on the expected change in heart rate, such as the expected change in heart rate is increasing, decreasing, or unchanging based on a change in motion by the user.

In a specific example, the device further includes a processing component. In one example, the processing component can be a processor. In at least one example, the processing component can include both a processor and a memory. In at least one example, the processor can be an embedded Advanced Reduced Instruction Set Computer (RISC) machine (ARM) micro-processing unit. The processing component can be configured to separate the detected signal into its constituents. In one example, the processing component is configured to separate the signal into its constituents or signal components. In at least one example, the constituents can be a portion of the vector, as described above. The device can be configured to transmit an alert to an output device, which can include a speaker, a vibrator, a display, or light. The optical-electronic device can be further configured to communicate a level of a biological indicator to a user in real-time. In a further example, the device can be configured to determine the heart rate of the user during exercise and other physical conditions.

The device can be configured to determine physiological parameters of a user during exercise. It is to be understood, however, that the device can also be used in other applications without departing from the principles of the present disclosure, including microcirculation analysis, newborn perfusion deficit, assessment of hemorrhage and shock, monitoring of fluid resuscitation, cognitive studies, cerebral oxygenation monitoring during cardiothoracic procedures, muscular oxygenation monitoring to diagnose acute and chronic compartment syndrome, and the monitoring of coronary artery disease (CAD) and other cardiovascular diseases.

The present disclosure generally relates to a non-invasive optical-electronic device configured to measure physiological parameters of a user. In at least one example, the device is configured to measure the heart rate of the user. The device can further include at least one emitter configured for emitting at least one wavelength to a tissue of the user and a photodetector configured to detect at least one reflected light signal from the tissue. In at least one example, the emitter(s) can emit at least two different wavelengths. The device further includes a processing component configured to calculate a combination of the detected light signals, separate the combination of detected light signals into signal components, and apply a filter to the to the signal components. In at least one example, the device optionally includes a motion detector to detect a motion signal from the user and the motion signal is further combined with the signal components using a Bayesian filter with the processing component. In at least one example, processing component can be configured to remove motion artifacts in the filter. In this example, the peaks of the motion signal can assist in determining the true peaks in the input signal. The device can be configured to transmit an alert to an output device. The optical-electronic device can be further configured to communicate a level of biological indicator to a user in real-time.

In at least one example, an optical-electronic device can be configured to determine the level of one or more biological indicators during exercise and other physical conditions is provided.

In at least one example, a device configured to determine the level of a biological indicator within tissues or vessels is provided. The device includes at least two emitters configured to emit light into a tissue. The emitters can emit light at the same or different wavelengths. The device can optionally include a motion detector to detect a motion signal from the user. For example, the motion detector can be a gyroscope or an accelerometer. The device further includes a photodetector configured to detect the light back-scattered from the tissue and transmitting data representative of the received reflected light. In various examples, the at least two wavelengths are within a range of about 450 nm to about 1100 nm, about 450 nm to about 660 nm, and about 550 nm to about 950 nm. In some examples, at least three wavelengths are emitted and at least three reflected light signals are detected. Non-limiting examples of emitted wavelengths include, but are not limited to 505 nm, 470 nm, 630 nm, 550 nm, 650 nm, 950 nm, 1100 nm, and combinations thereof. In at least one example, 505 nm may be preferred over 640 nm which may be preferred over 470 nm. In the second example, 550 nm may be preferred over 950 nm which may be preferred over 650 nm. While these wavelengths are provided, the present disclosure includes wavelengths within one or more of the above ranges.

The device further includes a processing component configured to process the data representative of the detected reflected light and any motion signals. In at least one example, the processing component is a hardware processor, and in another example, the processing component includes a processor and a non-transitory storage medium configured to store instructions to cause the processor to receive the data representative of the received reflected light. The processor can also be instructed to calculate a combination of the detected reflected light signals. The processor can also be instructed to estimate the heart rate of the user based on the combination. The processor can also be instructed to transmit heart rate to an output device. The processor can also be instructed to transmit an alert to an output device. In at least one example the linear combination weights can be selected from a finite set of values (for example, −1, 0 and 1) and the exhaustive search of values can then be performed by calculating the performance obtained by selecting every possible weight applied to every signal. For a set of n input signals and m different weight values, this corresponds to measuring the performance of each one of the $n^m$ combinations and selecting the one that provides us with at least significantly better performance.

In at least one example, a calibration method for converting optical data into a parameter corresponding to the attenuation properties of a biological tissue is provided. The method includes generating a calibration factor to convert detected light into optical densities for a given current. The calibration factor is measured by transmitting light through a stable phantom of known optical properties. The method can also include emitting light from at least two emitters into a tissue, where the two emitters are separated by a known distance. The method can include receiving detected light data and current from the tissue at a photodetector. The method can also include converting detected light data into optical densities for a given current using the calibration factor. The method can include converting the optical densities into effective attenuation coefficients using optical densities determined from light data received from the two emitters separated by a known distance. The method can also include converting the effective attenuation coefficients into absorption coefficients using a reduced scattering coefficient obtained for the tissue being monitored, where the absorption coefficient corresponds to the attenuation properties of the tissue.

In at least one example, a method of calibrating optical data can be used to determine a level of a biological indicator. As used herein, a level of a biological indicator means a measurement or other data that is useful to a user. A biological indicator can include one or more of a heart rate, a lactate threshold, or blood oxygenation. The method includes generating a calibration factor to convert detected light into optical densities for a given current and emitting light from at least two emitters into a tissue, where the at least two emitters are separated by a known distance. A calibration factor, as used herein, refers to the measured value obtained by transmitting light through a stable phantom of known optical properties. The method can also include converting detected light data into optical densities for a given current using the calibration factor. The method can include converting the optical densities into effective attenuation coefficients. The method can also include converting the effective attenuation coefficients into absorption coefficients ($\mu_a$) using a reduced scattering coefficient ($\mu_s'$) obtained for the tissue being monitored, wherein the absorption coefficient corresponds to the attenuation properties of the tissue, and using the relative match of the absorption coefficient to predetermined spectral data to determine the level of a biological indicator in tissue. The method can further include communicating the level of a biological indicator to a user in real-time.

In at least one example, a method of determining a user-specific measure of a biological indicator in a tissue using a predetermined set of user-specific parameters is provided. The method includes generating a set of user-specific parameters based on that user's biological indicator data collected during an assessment using an optical-electronic device configured to capture optical data and motion data of a tissue. The method can also include storing the set of user-specific parameters on a server. The method can include measuring a biological indicator in the tissue of the user during a physical activity using an optical-electronic device configured to capture the optical data of a tissue. The method can also include calculating a user-specific measure of the biological indicator using the set of user-specific parameters stored on the server. The method can further include transmitting an alert to an output device, wherein the alert is configured to notify the user of a user-specific measure of biological indicator. The method can further include communicating a level of a biological indicator to a user in real-time.

In at least one example, a method of non-invasive tissue monitoring is disclosed. Additionally, the method can include using optical signals to determine the user's heart rate is provided. The method includes receiving at least one reflected light signal from a user after emitting light having at least one wavelength directed at the user. The method contemplates processing of the optical signals, and further includes calculating a combination of at least two detected light signals. The at least two detected light signals can be reflected signals from at least two different wavelengths of emitted light. The combination of detected light signals can be used to perform one or more of the following: oxygenation monitoring, photoplethysmograph (PPG) detection, heart rate monitoring, motion detection, total hemoglobin monitoring, respiration monitoring, or hydration monitoring. In one example, the at least two wavelengths are in the range of 600 to 1100 nm, which provides deep tissue monitoring because of the low light absorption of tissue within this range, and also because this range is within the Silicon photodiode detection window. In another example, the wavelengths are within the range 450 nm to 660 nm, which provides shallow tissue monitoring and ambient light blocking because of the relatively high light absorption of tissue within this range. In a further example, the wavelengths are within the range 450 nm to 1100 nm, encompassing the entire range of light absorption available to Silicon photodetectors.

In at least one example, the method for tissue monitoring can further include separating the detected signal into its main components. The separation of signals is performed to select at one or more of the following: oxygenation monitoring, PPG detection, heart rate monitoring, motion detection, total hemoglobin monitoring, respiration monitoring, or hydration monitoring.

In at least one example, the method for tissue monitoring can further include receiving a motion signal from a motion detector, such as a gyroscope or an accelerometer.

In at least one example, the method for tissue monitoring can further include optimizing the combination of signals for each user, resulting in personalized signals that are configured to monitor the heart rate of an individual. For example, a search can be performed to find the combination that works best for a given individual after he/she has collected data while wearing an EKG monitor.

In another example, the personalized optimization of the combination can be performed multiple times for the same user, resulting in heart rate monitoring that responds to physiological changes over time. The method can further include updating the estimate of the heart rate of the user. An expected change in the heart rate can be determined using the motion signal. In at least one example, the estimated heart rate can be updated based on the expected change in heart rate, such as the expected change in heart rate is increasing, decreasing, or unchanging based on a change in motion by the user.

In at least one example, the separation of signals is performed using a bank of filters. The bank of filters can include one or more of finite impulse response filters, frequency-domain filters, or wavelength domain filters. In at least one example, all filters are k-wavelengths deep.

In another example, the separation of signals is performed using at least one adaptive filter. The adaptive filters can include one or more of a Kalman filter, a Bayesian filter, a least-mean-squares filter, or a root-mean-squares filter. The present disclosure includes at least one example of an adaptive filter used to cancel out motion data from the detected optical data using adaptive weights W that are iteratively adjusted so that the filtered optical data contains most of the heart rate information with little interfering motion data to confuse the heart rate estimation algorithm (a filter bank in this example).

In another example, the separation of signals is performed using at least one fixed filters. The method can utilize a low-pass filter(s) for detecting the slowly varying signals such as oxygenation, hydration and total hemoglobin. The method can utilize a band pass filter(s) for detecting the more rapidly varying signals such as the PPG, heart rate and motion. The band pass filters can be distinct (optimized to each specific signal) or identical (detecting several signals within the same range of frequencies). The method can utilize a high pass filter(s) for detecting motion and noise since these signals also occur at frequencies higher than those frequencies of interest for most biological processes.

In another example, the separation of signals is performed using motion data from an inertial measurement unit (IMU), and the data from the IMU is used to separate motion from physiological data. Further, the motion data from the IMU can be cross-correlated with data from a PPG measurement to remove motion. This is also known as the Wiener solution. In at least one example, the Wiener solution can be adapted to use IMU and PPG data as input signals.

In another example, the separation of signals can be performed using an autocorrelation of the combination. Then, a peak of the autocorrelation signal can be used to detect a heart rate.

In another example, the separation of signals is performed using at one or more of the following: short-time Fast Fourier Transforms, tone-detection, or mean-absolute difference autocorrelation.

In at least one example, a device configured to monitor tissue and detect heart rate, using near-infrared light, is disclosed. The device includes at least one emitter configured to emit light having at least two different wavelengths, a photodetector configured to detect at least one reflected light signal, and a processing component configured to calculate a combination of the detected light signals. In one example, the photodetector is configured to detect at least three light signals reflected from the emission of at least three different wavelengths from the emitter(s). The calculated combination is a linear combination in one example. The combination can be used to perform one or more of the following: oxygenation monitoring, PPG detection, heart rate detection, motion detection, total hemoglobin detection, or hydration detection.

The device can further include a motion detector to detect a motion signal from the user. For example, the motion detector can be a gyroscope or an accelerometer. The processing component can be further configured to combine the detected light signals with the motion signal to estimate the user's heart rate. In at least one example, the combination of detected light signals may first be separated into its signal components before being combined with the motion signal. In one example, the signal components and the motion signal can be combined using a Bayesian filter.

The processing component can further be configured to repeat the steps above after a period of time and update the estimate of the heart rate of the user. An expected change in the heart rate can be determined using the motion signal. In at least one example, the estimated heart rate can be updated based on the expected change in heart rate, such as the expected change in heart rate is increasing, decreasing, or unchanging based on a change in motion by the user.

In one example, the at least two wavelengths are in the range of 600 nm to 1100 nm, which provides deep tissue monitoring within the Silicon photodiode detection window. In another example, the wavelengths are within the range of 450 nm to 660 nm, which provides shallow tissue monitoring and ambient light blocking. In a further example, the wavelengths are within the range of 450 nm to 1100 nm.

The device can further include a processing component configured to separate the detected signal into its main components. The separation of signals is performed to select one or more of the following: oxygenation monitoring, PPG monitoring, heart rate monitoring, motion detection, total hemoglobin monitoring, respiration monitoring, or hydration monitoring.

In at least one example, the device can further include optimizing the combination of signals for each user, resulting in signals that are personalized for the particular user so that the heart rate of an individual can be monitored.

In another example, the personalized optimization of the combination can be performed multiple times for the same user, resulting in heart rate monitoring that responds to physiological changes over time. In at least one example, the personalized optimization is performed a minimum of two times.

In at least one example, the separation of signals is performed using a bank of filters. The bank of filters can include one or more of finite impulse response filters, Frequency-domain filters, or wavelength domain filters. In at least one example, all filters are k-wavelengths deep.

In another example, the separation of signals is performed using at least one adaptive filter. The adaptive filters can include one or more of a Kalman filter, a Bayesian filter, a least-mean-squares filter, or a root-mean-squares filter.

In another example, the separation of signals is performed using at least one fixed filter. The method can utilize a low-pass filter(s) for detecting oxygenation, hydration and total hemoglobin. The method can utilize a band pass filter(s) for detecting PPG, heart rate and motion. The band pass filters can be distinct or identical. The method can utilize a high pass filter(s) for detecting motion and noise.

In another example, the separation of signals is performed using motion data from an IMU, and the data from the IMU is used to separate motion from physiological data. Further, the motion data from the IMU can be cross-correlated with data from a PPG measurement to remove motion. This is also known as the Wiener solution.

In another example, the separation of signals can be performed using an autocorrelation of the combination. Then, the heart rate frequency is inversely proportional to the temporal separation between the central and adjacent peak of the auto-correlation signal.

In another example, the separation of signals is performed using one or more of the following: short-time Fast Fourier Transforms, tone-detection, or mean-absolute difference autocorrelation.

The device can be used for monitoring at least one of tissue oxygenation, the PPG waveform, heart rate, motion, total hemoglobin or hydration. In a further example, the device can be configured to transmit an alert to an output device. The device can be further configured to communicate a level of biological indicator to a user in real-time. Further, the device can be configured to transmit the optical signals it detects wirelessly, through a wire to another device, to the cloud or to a server wherein the signals can be processed and/or stored.

FIG. 1 illustrates a non-invasive optical-electronic device 100, according to an example of this disclosure. The device 100 can be attached to a portion of a user via a strap 115. The portion of the user that the device 100 is attached can be a plurality of locations including a muscle mass such as the leg or arm of the user. In other examples, the portion of the user that the device 100 is attached can be a wrist, a head, an ankle, neck, or chest, or other portion of the user. In one example, the portion of the user that the device is attached can be the wrist for accessibility and ease of use. The device 100 can be used with an optional output device 150, such as a smartphone (as shown), a smart watch, computer, mobile phone, tablet, a generic electronic processing and displaying unit, cloud storage, or a remote data repository via a cellular network or wireless Internet connection.

The device 100 includes a sensor 125 that is configured to determine the level of a biological indicator within tissue or blood vessels using NIRS. The sensor 125 includes an optical emitter 105 and an optical detector 110. In general, the sensor 125 uses two or more low-power lasers, light emitting diodes (LEDs) or quasi-monochromatic light sources and low-noise photodetecting electronics to determine the optical absorption of chromophores, such as water, hemoglobin in its multiple forms, including oxyhemoglobin (HbO2), deoxyhemoglobin (HHb), oxymyoglobin, deoxymyoglobin, cytochrome c, lipids, melanins, lactate, glucose, myoglobin (including myoglobin at least one of oxymyoglobin, deoxymyoglobin, and total myoglobin) or metabolites. The metabolites can include at least one of lactate and lactic acid. Cytochrome c can be used, for example, to track muscle adaptation to training. In another example, the sensor 125 can use a broad-spectrum optical source and a detector sensitive to the spectral components of light, such as a spectrometer, or a charge-coupled device (CCD) or other linear photodetector coupled with near-infrared optical filters.

The optical-electronic device 100 can be configured to include a second sensor 135 configured to measure photoplethysmography (PPT) of the user. The second sensor 135 includes an optical emitter 145 and an optical detector 146. The device 100 also includes a third sensor 175 configured to measure electrocardiography (EKG) and derived systolic time intervals (STI) of the user. The third sensor 175 includes a first electrode 180 and a second electrode 181. The sensors 125, 135, 175 in the device 100 can measure NIRS parameters, electrocardiography, photoplethysmography, and derived systolic time intervals (STI) of the user. The optical-electronic device 100 also includes a processor that is configured to analyze data generated by the sensors 125, 135, 175 to determine a cardiac response to exercise and the supply, arteriovenous difference, utilization of oxygen by the muscle tissue and hydration of the muscular tissue.

In at least one example, the processor is configured to determine biological indicators, including, but not limited to a relative percentage, a saturation level, an absolute concentration, a rate of change, an index relative to a training threshold, and a threshold. In other cases, the processor is configured to determine perfusion characteristics such as pulsatile rhythm, blood volume, vascular tone, muscle tone, and angiogenesis from total hemoglobin and water measurements.

The device 100 can include a power supply, such as a battery, to supply power to the sensors 125, 135, 175 and other components in the device 100. In one example, the sensor 125 has a skin contact area of 3.5"×2". In other examples, the device 100 can be sized to be on the user's wrist so that there is a skin contact area of 1.5"×1.5". Additionally, other changes in dimensions are considered within the scope of this disclosure.

Figure 2A:
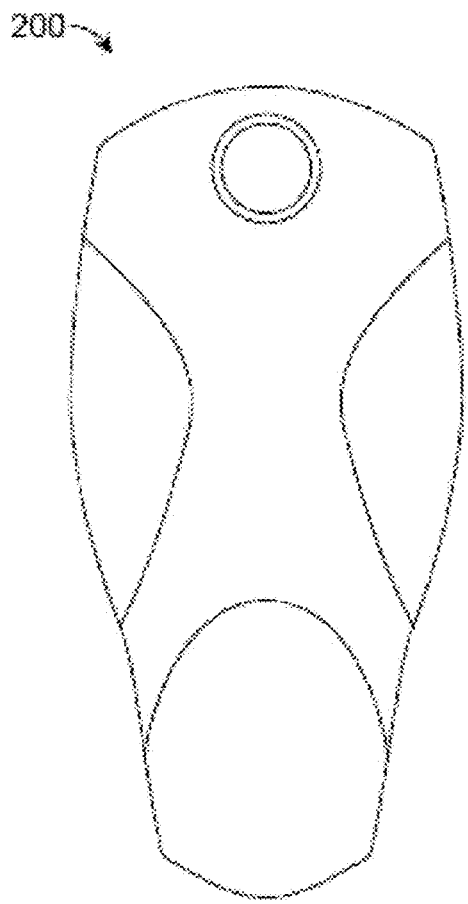
FIG. 2A is a schematic diagram of the front of a non-invasive tissue monitoring device according to an example of the present disclosure.
Figure 2B:
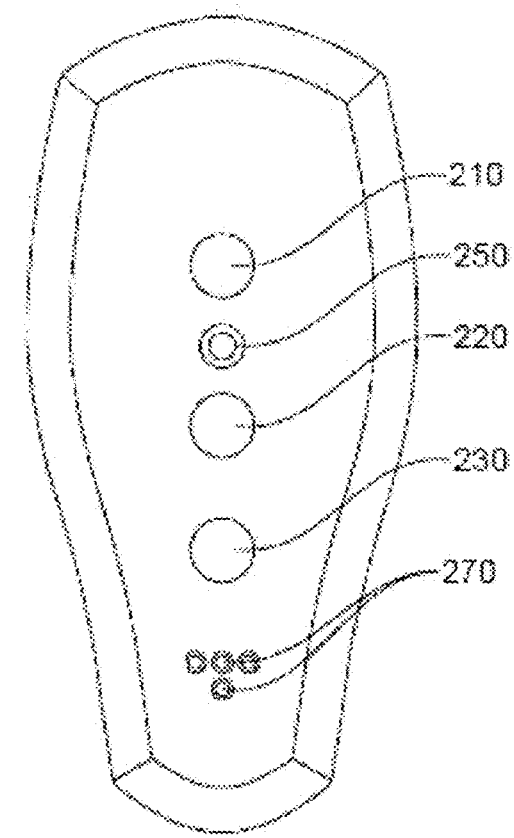
FIG. 2B is a schematic diagram of the back of a non-invasive tissue-monitoring device according to an example of the present disclosure.

FIG. 2 illustrates a non-invasive optical-electronic device 200, according to an alternative example of this disclosure. The device 200 is configured to be worn on a limb of a user, such as on the calf muscle of a user's leg or the bicep of a user's arm. In at least one example, the device 200 can be optimized to a given limb for increased accuracy. In other examples, the device 200 can be optimized based on the size, gender, or age of the user. In still other examples, a variety of the above optimizations can be implemented for a given device. FIG. 2A illustrates the front of the optical-electronic device. FIG. 2B illustrates the back of the optical-electronic device, including emitters 220, 230, 250 and photodetector 210. The device 200 also includes data and charging contacts 270. In at least one example, the data and charging contacts 270 can be used to electrically detect if the sensor is making contact with the skin of a user. The presence of multiple emitters 220, 230, 250 on the optical-electronic device allows for spatially-resolved data gathering in real-time. The optical-electronic device 200 can be configured to determine the optical absorption of chromophores, such as water, hemoglobin in its multiple forms, including oxyhemoglobin (HbO2), deoxyhemoglobin (HHb), oxymyoglobin, deoxymyoglobin, cytochrome c, lipids, melanins, lactate, glucose, or metabolites.

Figure 2C:
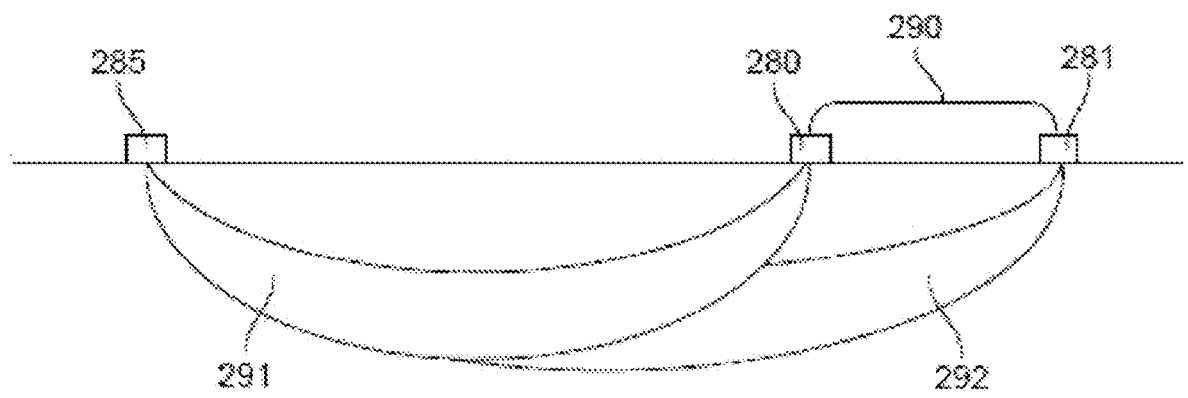
FIG. 2C is a schematic diagram of a spatially-resolved near-infrared spectroscopy (NIRS) sensor that is included on a non-invasive tissue-monitoring device according to an example of the present disclosure.

FIG. 2C illustrates a spatially-resolved NIRS sensor that can be included on the non-invasive optical-electronic device 200, according to an example of the disclosure. As shown in FIG. 2C, the spatially-resolved NIRS sensor includes light emitters 280 and 281 which emit light that is scattered and partially absorbed by the tissue. Each emitter 280, 281 can be configured to emit a single wavelength of light or a single range of wavelengths. In at least one example, each emitter 280, 281 can be configured to emit at least three wavelengths of light or at least three ranges of wavelengths. Each emitter 280, 281 can include one or more light emitting diodes (LEDs). Each emitter 280, 281 can include a low-powered laser, LED, or a quasi-monochromatic light source, or any combination thereof. Each emitter 280, 281 can also include a light filter.

A fraction of the light emitted by emitters 280 and 281 is detected by photodetector 285, as illustrated by the parabolic or "banana shaped" light arcs 291 and 292. Emitters 280, 281, are separated by a known distance 290 and produce a signal that is later detected at photodetector 285. The detected signal is used to estimate the effective attenuation and absorption coefficients of the underlying tissue as described later in FIG. 6, for example at blocks 640 and 650. In at least one example, the known distance 290 is 12 mm. In other examples, the known distance can be selected based on a variety of factors, which can include the wavelength of the light, the tissue involved, or the age of the user.

The optical-electronic device 200 disclosed herein can have different numbers of emitters and photodetectors without departing from the principles of the present disclosure. Further, the emitters and photodetectors can be interchanged without departing from the principles of the present disclosure. Additionally, the wavelengths produced by the LEDs can be the same for each emitter or can be different.

In at least one example, the device 200 is used for the monitoring of physiological parameters of a user during a physical activity. Use of the device 200 is particularly relevant in endurance type sports, such as running, cycling, multisport competition, rowing, but can also be used in other physical activities. The device 200 can be configured to wirelessly measure real-time muscle parameters during physical exercise. The device 200 can be secured to a selected muscle group of the user, such as the leg muscles of the vastus lateralis or gastrocnemius, which are primary muscle groups of running and cycling.

Figure 3:
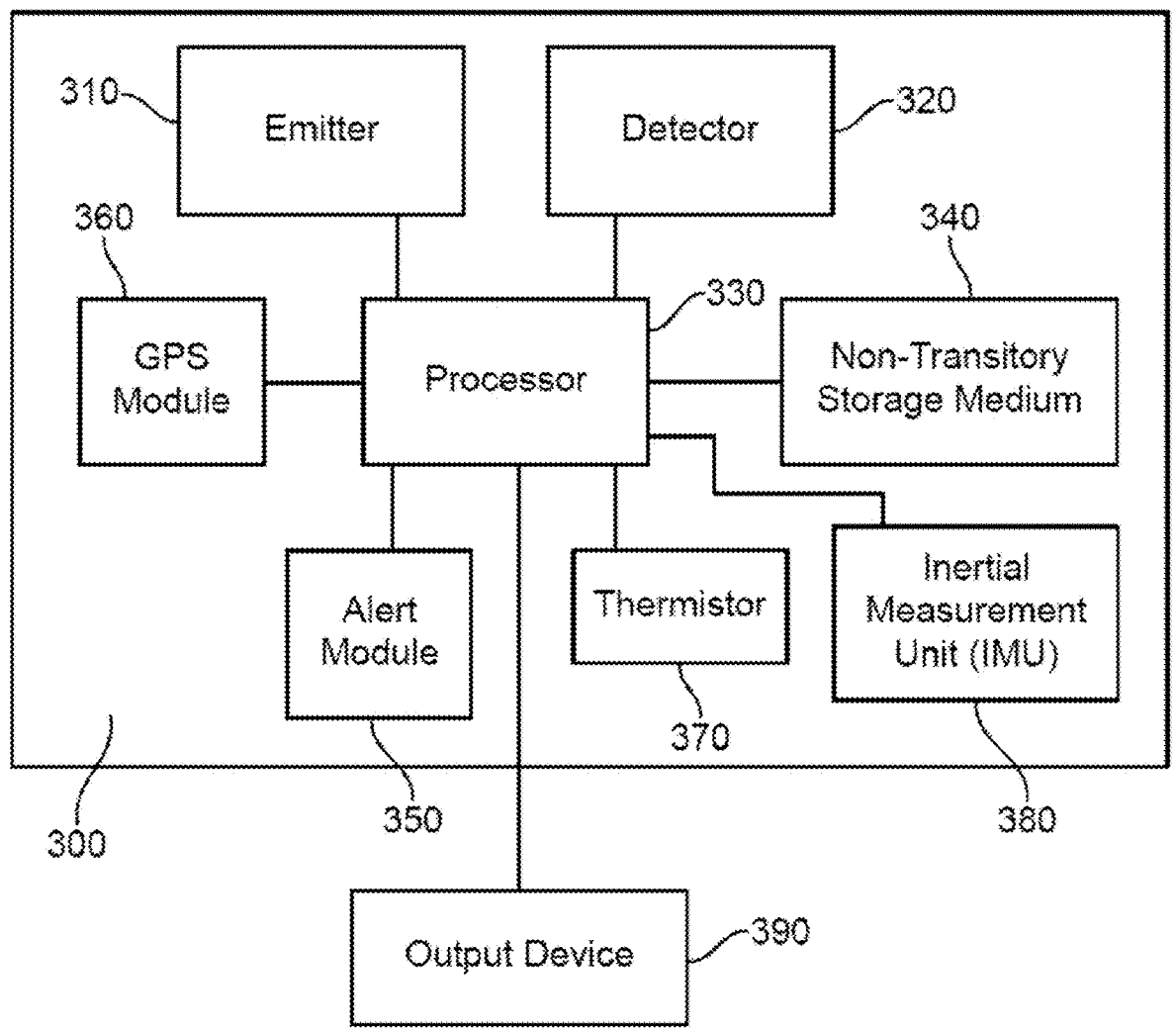
FIG. 3 is a block diagram of a tissue-monitoring device according to an example of the present disclosure.

FIG. 3 illustrates the components of an optical-electronic device 300 according to an example of this disclosure. As shown in FIG. 3, the optical-electronic device includes an emitter 310 and detector 320, which are coupled to a processor 330. The processor 330 is coupled to a non-transitory storage medium 340. The device 300 is coupled to an output device 390.

The emitter 310 delivers light to the tissue and the detector 320 collects the optically attenuated signal that is back-scattered from the tissue. In at least one example, the emitter 310 can be configured to emit at least three separate wavelengths of light. In another example, the emitter 310 can be configured to emit at least three separate bands or ranges of wavelengths. In at least one example, the emitter 310 can include one or more light emitting diodes (LEDs). The emitter 310 can also include a light filter. The emitter 310 can include a low-powered laser, LED, or a quasi-monochromatic light source, or any combination thereof. The emitter can emit light ranging from infrared to ultraviolet light. As indicated above, the present disclosure uses NIRS as a primary example and the other types of light can be implemented in other examples and the description as it relates to NIRS does not limit the present disclosure in any way to prevent the use of the other wavelengths of light.

The data generated by the detector 320 can be processed by the processor 330, such as a computer processor, according to instructions stored in the non-transitory storage medium 340 coupled to the processor. The processed data can be communicated to the output device 390 for storage or display to a user. The displayed processed data can be manipulated by the user using control buttons or touch screen controls on the output device 390.

The optical-electronic device 300 can include an alert module 350 configured to generate an alert. The processor 330 can send the alert to the output device 390 or the alert module 350 can send the alert directly to the output device 390. In at least one example, the optical-electronic device 300 can be configured so that the processor 330 is configured to send an alert to the output device 390 without the device including an alert module 350.

The alert can provide notice to a user, via a speaker or display on the output device 390, of a change in biological indicator conditions or other parameter being monitored by the device 300, or the alert can be used to provide an updated biological indicator level to a user. In at least one example, the alert can be manifested as an auditory signal, a visual signal, a vibratory signal, or combinations thereof. In at least one example, an alert can be sent by the processor 330 when a predetermined biological indicator event occurs during a physical activity.

In at least one example, the optical-electronic device 300 can include a Global Positioning System (GPS) module 360 configured to determine geographic position and tagging the biological indicator data with location-specific information. The optical-electronic device 300 can also include a thermistor 370 and an IMU 380. The IMU 380 can be used to measure, for example, gait performance of a runner or pedal kinematics of a cyclist, as well as physiological parameters of a user during a physical activity. The thermistor 370 and IMU 380 can also serve as independent sensors configured to independently measure parameters of physiological threshold. The thermistor 370 and IMU 380 can also be used in further algorithms to process or filter the optical signal.

Figure 4:
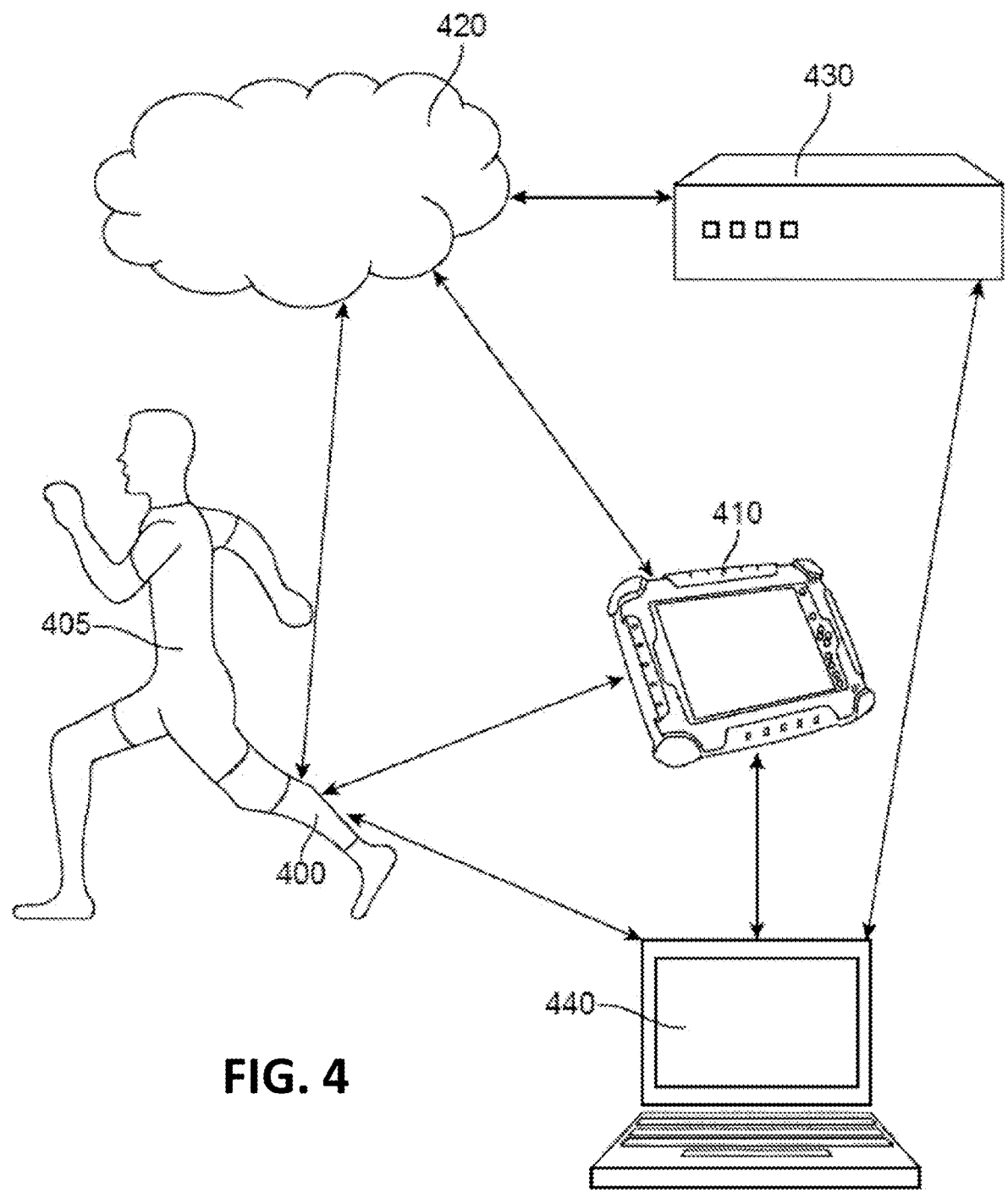
FIG. 4 is a schematic diagram of an environment within which the noninvasive tissue-monitoring device can be implemented, according to an example of this disclosure.

FIG. 4 illustrates an environment within which the non-invasive optical-electronic device 400 can be implemented, according to an example of this disclosure. As shown in FIG. 4, the optical-electronic device 400 is worn by a user to determine biological indicator levels during a physical activity. The optical-electronic device 400 is depicted as being worn on the calf of a user 405, however, the optical-electronic device 400 can be worn on any portion of the user suitable for monitoring biological indicator levels. The device 400 can be used with an output device 410, such as a smartphone (as shown), a smart watch, computer, mobile phone, tablet, a generic electronic processing and displaying unit, cloud storage, or a remote data repository via a cellular network or wireless Internet connection.

As shown in FIG. 4, the optical-electronic device 400 communicates with a output device 410 so that data collected by the optical-electronic device 400 is displayed or transferred to the output device 410 for communication of real-time biological indicator data to the user 405. In at least one example, an alert can be communicated from the device 400 to the output device 410 so that the user 405 can be notified of a biological indicator event. Communication between the device 400 and the output device 410 can be via a wireless technology, such as BLUETOOTH®, infrared technology, or radio technology, or can be through a wire. Transfer of data between the optical-electronic device 400 and the output device 410 can also be via removable storage media, such as a secure digital (SD) card. In at least one example, a generic display unit can be substituted for the output device 410.

The optical-electronic device 400 also communicates with a personal computing device 440 or other device configured to store or display user-specific biological indicator data. The personal computing device 440 can include a desktop computer, laptop computer, tablet, smartphone, smart watch, or other similar device. Communication between the device 400 and the personal computing device 440 can be via a wireless technology, such as BLUETOOTH®, infrared technology, or radio technology. In other examples, the communication between the device 400 and the personal computing device 440 can be through a wire or other physical connection. Transfer of data between the optical-electronic device 400 and the personal computing device 440 can also be via removable storage media, such as an SD card.

The output device 410 can communicate with a server 430 via a network 420, allowing transfer of user-specific biological indicator data to the server 430. The output device 410 can also communicate user-specific biological indicator data to cloud-based computer services or cloud-based data clusters via the network 420. The output device 410 can also synchronize user-specific biological indicator data with a personal computing device 440 or other device configured to store or display user-specific biological indicator data. The output device 410 can also synchronize user-specific biological indicator data with a personal computing device 440 or other device configured to both store and display user-specific biological indicator data. Alternatively, the personal computing device 440 can receive data from a server 430 or cloud-based computing service via the network 420.

The personal computing device 440 can communicate with a server 430 via a network 420, allowing the transfer of user-specific biological indicator data to the server 430. The personal computing device 440 can also communicate user-specific biological indicator data to cloud-based computer services or cloud-based data clusters via the network 420. The personal computing device 440 can also synchronize user-specific biological indicator data with the output device 410 or other device configured to store or display user-specific biological indicator data.

The optical-electronic device 400 can also directly communicate data via the network 420 to a server 430 or cloud-based computing and data storage service. In at least one example, the device 400 can include a GPS module configured to communicate with GPS satellites (not shown) to obtain geographic position information.

The optical-electronic device 400 can be used by itself or in combination with other optical-electronic devices or biosensors. For example, the optical-electronic device 400 can be used in combination with heart rate (HR) biosensor devices, foot pod biosensor devices, and/or power meter biosensor devices. The optical-electronic device 400 can also be used in combination with ANT+™ wireless technology and devices that use ANT+™ wireless technology. The optical-electronic device 400 can be used to aggregate data collected by other biosensors including data collected by devices that use ANT+™ technologies. Aggregation of the biosensor data can be via a wireless technology, such as BLUETOOTH®, infrared technology, or radio technology, or can be through a wire.

The biosensor data aggregated by the optical-electronic device 400 can be communicated via a network 420 to a server 430 or to cloud-based computer services or cloud-based data clusters. The aggregated biosensor data can also be communicated from the optical-electronic device 400 to the output device 410 or personal computing device 440.

In at least one example, the optical-electronic device 400 can employ machine learning algorithms by comparing data collected in real-time with data for the same user previously stored on a server 430, output device 410, or in a cloud-based storage service. The machine learning algorithm can also be performed on or by any one of the output device 410, cloud-based computer service, server 430, or personal computing device 440, or any combination thereof.

According to this disclosure, determination of the level of a biological indicator within tissue or blood vessels is achieved by calculating a relative match, or indices, between the spectral data received at the detector with a predetermined spectral data set of one or more chromophores corresponding to the biological indicator. In at least one example, the predetermined spectral data set corresponds to the signal spectra of specific analytes that can be readily obtained from the literature. See for example, Analyt. Biochem. Vol 227, pp. 54-68 (1995). The relative match calculation is performed by calculating a projection of the spectral data set captured from a user in the direction of the predetermined spectral data set in order to calculate an index that reflects the proximity of the match. The spectral projection method can be used to calculate a relative percentage level of a biological indicator or, with proper calibration, can be used to calculate the absolute concentration of a biological indicator.

The spectral projection method of determining the level of a biological indicator can be implemented mathematically using the inner product method which will be explained, by way of example, using the Total Oxygenation Index (TOI) as the biological indicator of interest. TOI is the ratio of the oxygenated hemoglobin (HbO2) to total hemoglobin (tHb), where total hemoglobin (tHb) is equal to the combined concentrations of the oxygenated hemoglobin (HbO2) and the chromophore deoxygenated hemoglobin (HHb):

TOI=[HbO2]/[tHb] or TOI %=100*([HbO2]/[tHb]),
where [tHb]=[HbO2]+[HHb].

TOI, as used herein, includes the more specific parameter, SmO2, which is the muscle oxygen saturation. SmO2 can also be the tissue oxygen saturation determined from optical measurements of muscle tissue. Both oxygenated hemoglobin (HbO2) and deoxygenated hemoglobin (HHb) are chromophores for which a spectral data set can be predetermined. The notation O(D) can be used to denote the predetermined spectral data for oxyhemoglobin (deoxyhemoglobin) at the same wavelengths for which the spectral data set for a user was measured at the detector, and U can be used to denote the measured data set, including an effective attenuation ($\mu_{eff}$) or an effective absorption coefficient ($\mu_a$).

The inner product method of calculating the spectral projection can be calculated according to different mathematical methods, including, but not limited to, a direction cosine method, vector projection method, and a pseudo-inverse projection method:

Direction Cosine Method:

$$TOI = \frac{\langle U, O \rangle}{\left\langle U, O + D\sqrt{\frac{\langle O, O \rangle}{\langle D, D \rangle}} \right\rangle},$$

Vector Projection Method:

$$TOI = \frac{\langle U, O \rangle}{\left\langle U, O + D\sqrt{\frac{\langle O, O \rangle}{\langle D, D \rangle}} \right\rangle},$$

Pseudo-Inverse Projection Method:

$$TOI = \frac{\left\langle U, O - \frac{\langle O, D \rangle}{\langle D, D \rangle} D \right\rangle}{\left\langle U, O \left[ 1 - \frac{\langle O, D \rangle}{\langle D, D \rangle} \right] + D \left[ \frac{\langle O, O \rangle}{\langle D, D \rangle} - \frac{\langle O, D \rangle}{\langle D, D \rangle} \right] \right\rangle}.$$

All of these methods can be rewritten as $$TOI = \frac{\langle U, O - aD \rangle}{\langle U, O(1-a) + D(b-a) \rangle}$$

where a and b are scalars defined as i) $a = 0, b = \sqrt{\frac{\langle O, O \rangle}{\langle D, D \rangle}}$ ; ii) $a = 0, b = \frac{\langle O, O \rangle}{\langle D, D \rangle}$ ; and iii) $a = \frac{\langle O, D \rangle}{\langle D, D \rangle}$ and $b = \frac{\langle O, O \rangle}{\langle D, D \rangle}$ for the cosine, vector projection and pseudo-inverse methods, respectively.

Figure 5:
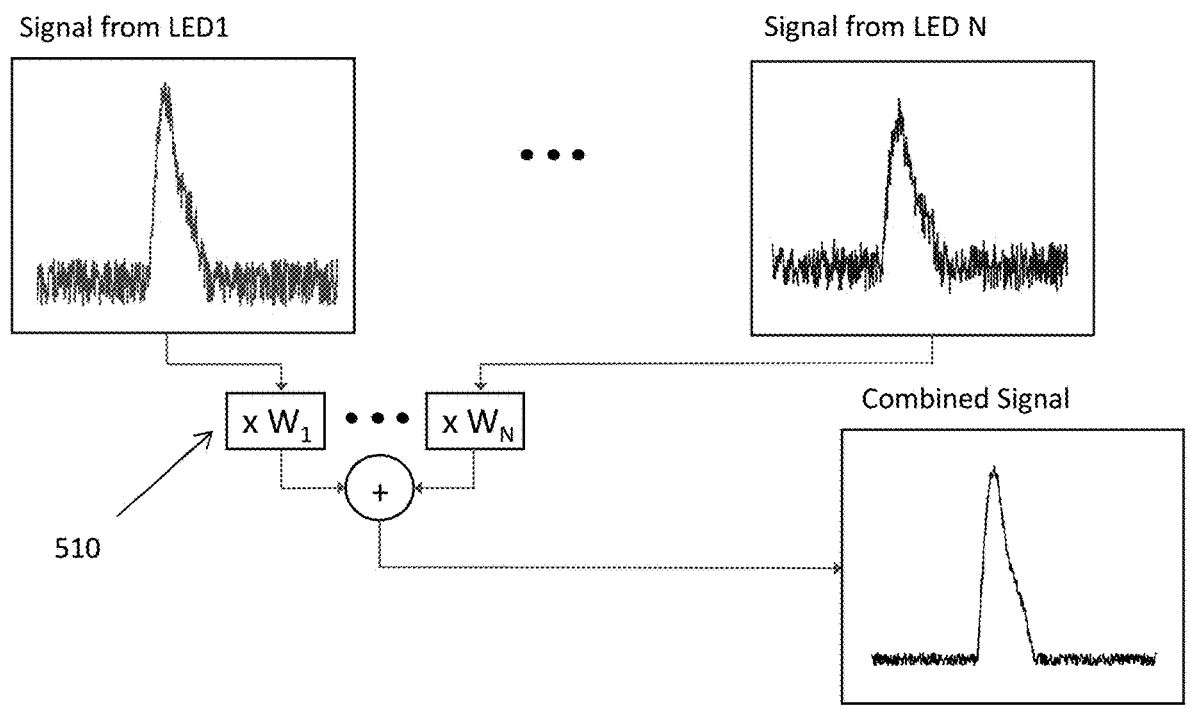
FIG. 5 is a block diagram depicting a way of removing noise from detected optical tissue monitoring signals, specifically linear combination of signals from two or more light emitting components.

FIG. 5 is a flowchart depicting a way of removing noise from detected optical tissue monitoring signals, specifically linear combination of signals from a plurality of light emitting components. As illustrated, the method obtains signals from a plurality of LEDs. The signals obtained from the LEDs are processed according to a formula 510, which can be a weighted function. The weighted function allows for certain signals to receive a greater importance as compared to other ones of the signals. The results of the formulas are added together to generate a single combined signal. The combined signal can be run through additional filters to remove noise sources that generate coherent noise (for example, motion, blood volume variations, and the like).

Figure 6:
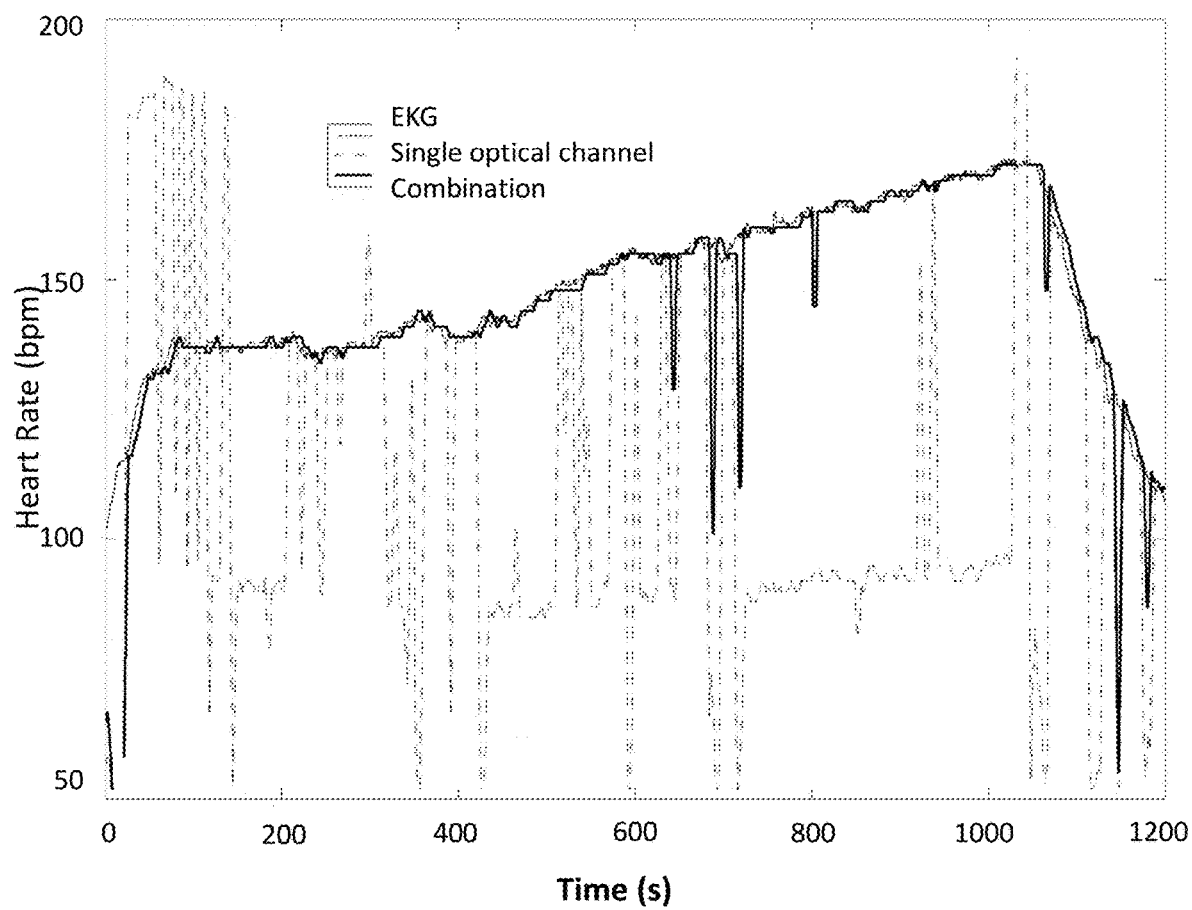
FIG. 6 is a plot illustrating the improvement in heart rate detection using the combination method according to this disclosure, as compared to the prior art method of using the signal from a single illumination source.

FIG. 6 is a plot illustrating the improvement in heart rate detection using a combination method according to this disclosure, as compared to a method of using the signal from a single illumination source. The heart rate estimates generated by both methods are compared to the signal detected by a commercially available EKG heart rate monitor. The "combination" signal in the plot (solid line) more closely matches the heart rate measurement generated by the EKG than the "single optical channel" signal (dotted line). In this example, the root-mean square (RMS) difference from the EKG value to the combination signal is 7 bpm compared to an RMS difference of 51 bpm for the single optical channel estimate.

Figure 7:
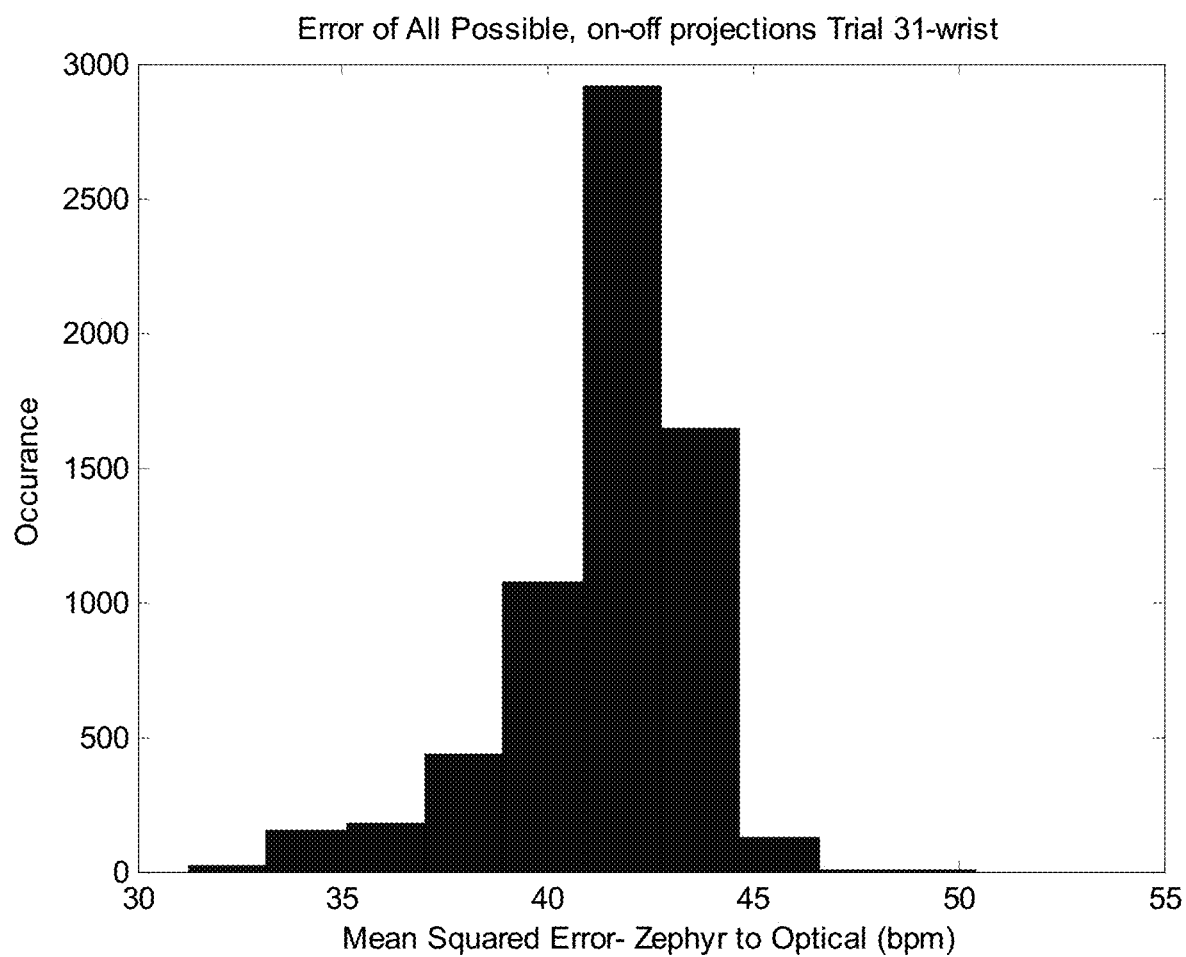
FIG. 7 is a plot demonstrating the error comparison between the removal of noise using a vector projection method according to this disclosure, as compared to a heart rate signal detected by a commercially available electrocardiogram (EKG) heart rate monitor.

FIG. 7 is a plot demonstrating the mean squared errors obtained using multiple combinations. A significantly better combination is one that results in a significant lower error when compared with other combinations. In yet other examples, the significantly better combination can be within a range of errors, which may be predetermined.

Figure 8:
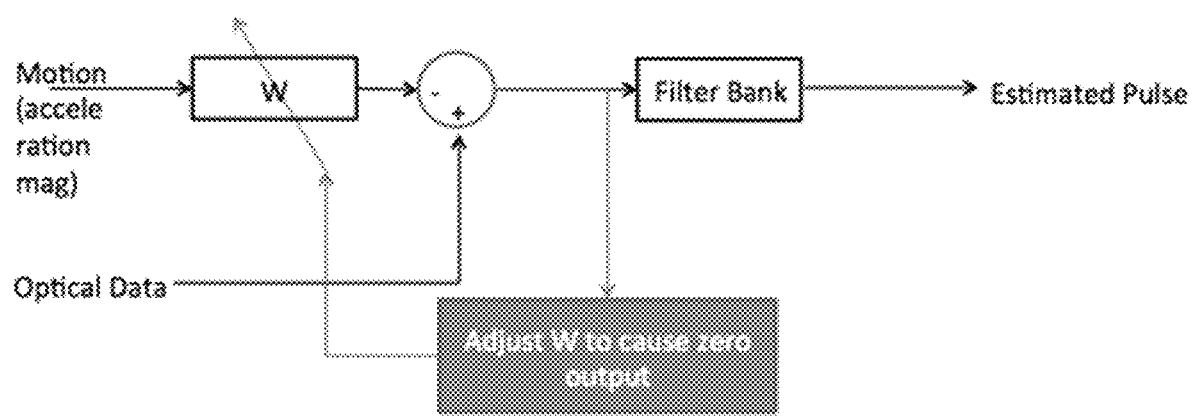
FIG. 8 is a block diagram depicting a method of adaptive filtering for separating signal components according to this disclosure.

FIG. 8 is a diagram depicting a method of adaptive filtering for separating signal components and performing adaptive noise cancelling according to this disclosure. "W" in the diagram is a weight vector that can be continuously adjusted by the device. The vector is multiplied by the motion vector (that is, either the acceleration, angular acceleration magnitude, or power) generated by the IMU is projected or multiplied towards the weight vector w. The vector multiplication is added to the combined optical data. The weighted measure can be continuously adjusted by the device using, for example, a gradient descent algorithm such as the least-mean squares (LMS) algorithm, the LMS-Newton algorithm, the normalized LMS algorithm or the transform-domain LMS algorithm, to attempt to reduce the acceleration magnitude to zero, and eliminate motion artifact from the heart rate measurement. The combined motion and optical signal is then sent through a filter bank to produce the output heart rate signal.

Figure 9:
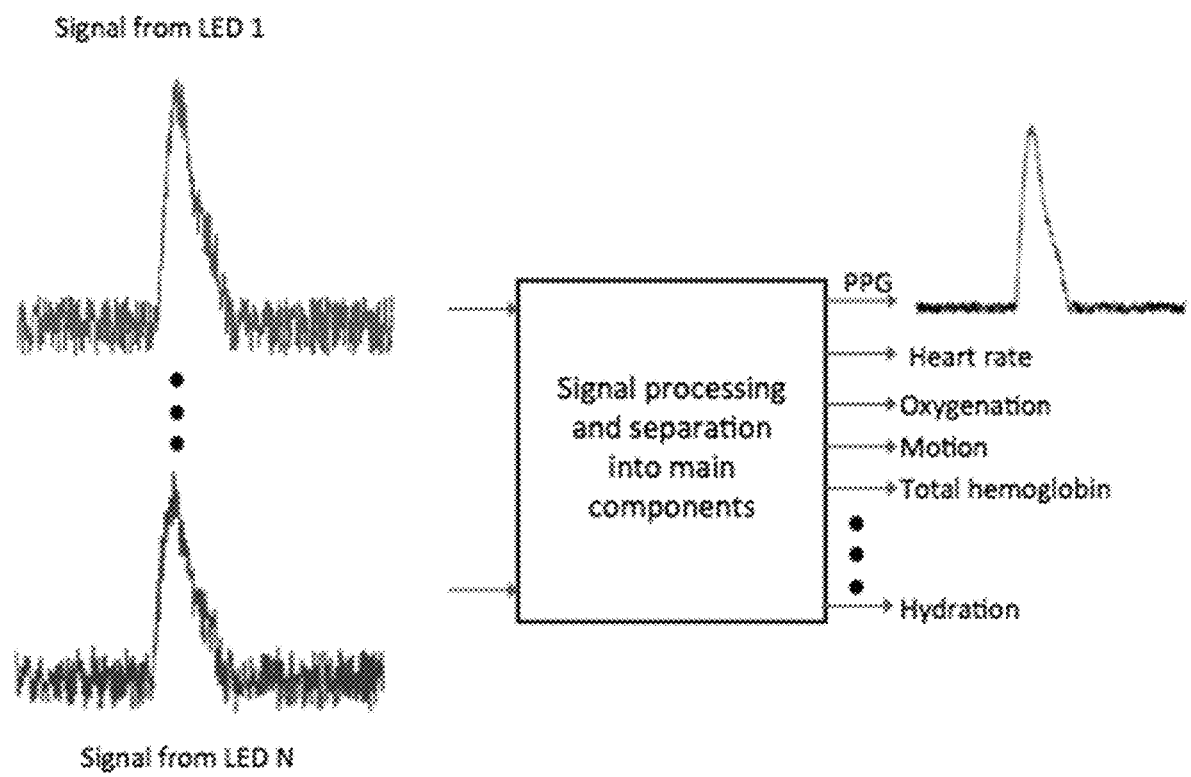
FIG. 9 is a schematic diagram depicting the separation of signals according to an example of this disclosure.

FIG. 9 is a diagram depicting the separation of signals according to an example of this disclosure. The optical signals from each LED are first combined and then separated into its constituents, or signal components, to monitor one or more of oxygenation monitoring, PPG detection, heart rate detection, motion detection, total hemoglobin detection, or hydration detection. The combination of signals provides a cleaner PPG signal. The heart rate signal can be obtained using the methods described herein. Alternatively, the heart rate signal component can be the input signal indicative of a heart rate used in combination with other heart rate detection methods described herein. The detection of chromophores such as oxyhemoglobin, deoxyhemoglobin and water, to name a few, can be performed using the method for detecting biological indicators described herein.

Figure 10:
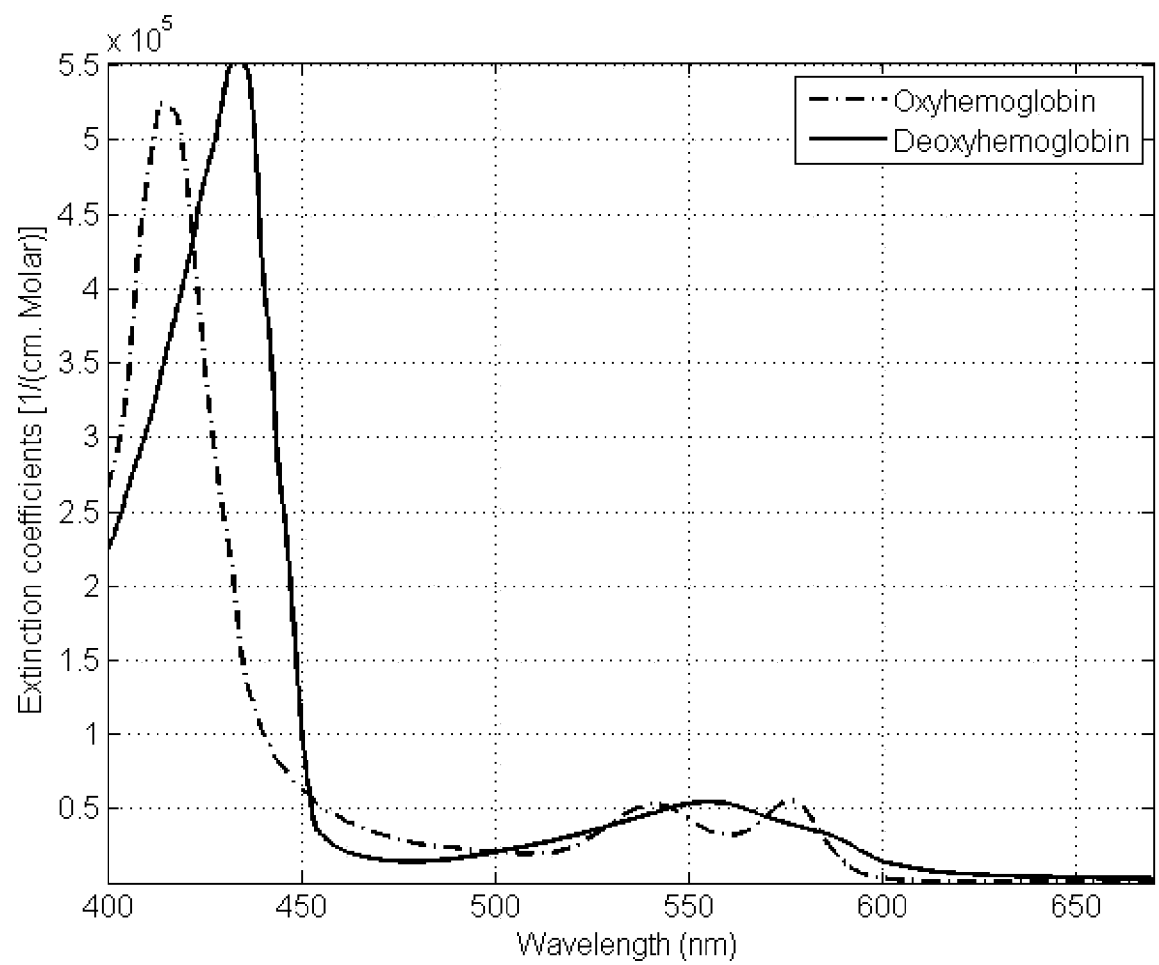
FIG. 10 is a plot of the extinction coefficients of deoxyhemoglobin and oxyhemoglobin as a function of wavelength over the visible range of wavelengths.

FIG. 10 is a plot of the extinction coefficients of deoxyhemoglobin and oxyhemoglobin as a function of wavelength over the visible range of wavelengths.

Figure 11:
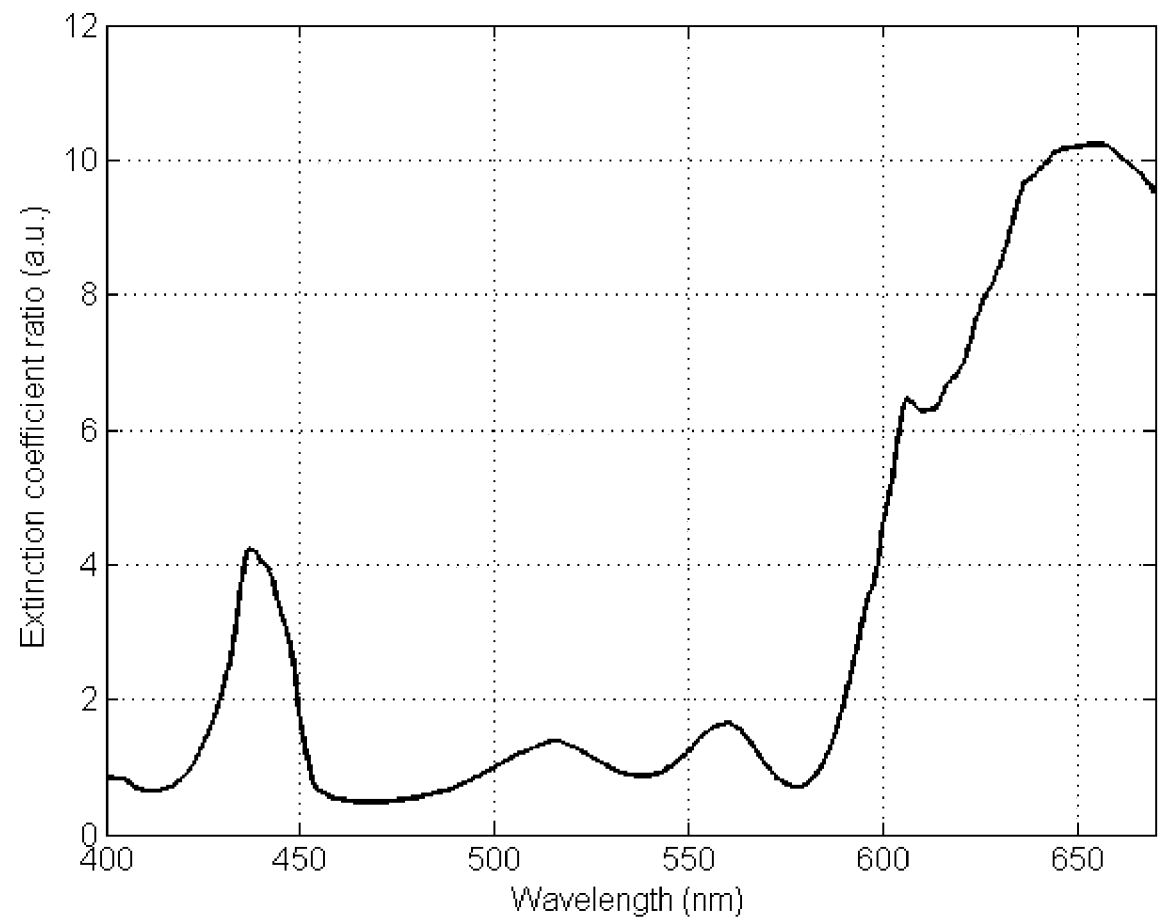
FIG. 11 is a plot of the ratio of the deoxyhemoglobin and oxyhemoglobin extinction coefficients as a function of wavelength over the visible range of wavelengths.

FIG. 11 is a plot of the ratio of the deoxyhemoglobin and oxyhemoglobin extinction coefficients as a function of wavelength over the visible range of wavelengths. The isobestic points are represented by the wavelengths in which the plot crosses unity. Of those points the one at 500 nm is of particular interest since it represents the isobestic point at which the local slope is smallest and, hence, the ratio is least sensitive to small deviations in wavelength. At least two points are needed in order to measure oxygen saturation. Hence, the peaks at 438 nm and 650 nm are of particular interest since they not only represent the largest peaks available within this wavelength ratio but also because they represent points wherein deoxyhemoglobin and oxyhemoglobin have inverted extinction coefficients (see FIG. 10).

The device disclosed herein can have different numbers of emitters and photodetectors without departing from the principles of the present disclosure. Further, the emitters and photodetectors can be interchanged without departing from the principles of the present disclosure. Additionally, the wavelengths produced by the LEDs can be the same for each emitter or can be different. In one example, the light emitting components emit light in the near infrared spectrum. In another example, the light emitting components emit light at wavelengths in the visible spectrum.

In one example, light is emitted by the light emitting components within the range of about 400 nm to about 950 nm. In one example, light is emitted by the light emitting components within the range of about 400 nm to about 650 nm. In one example, the wavelengths selected are 505 nm, 470 nm and 630 nm. These wavelengths are selected based on the plots in FIGS. 10 and 11. In another example, the light-emitting components can emit light at wavelengths selected from about 550 nm, about 950 nm, and about 650 nm. Without being limited to a particular theory, a wavelength of about 550 nm can be used for a high hemoglobin absorption region but may also affected by melanin concentration, a wavelength of about 950 nm can be used for a high water absorption region but may have low hemoglobin absorption and be weakly affected by melanin, and a wavelength of about 650 nm can be used for a large separation between oxy- and deoxyhemoglobin, enabling the determination of blood oxygenation. Since blood plasma is mostly water, a wavelength of about 950 nm can also work well in detecting heart rate, especially if combined with a wavelength of about 530 nm using the techniques described in this disclosure.

Figure 12:
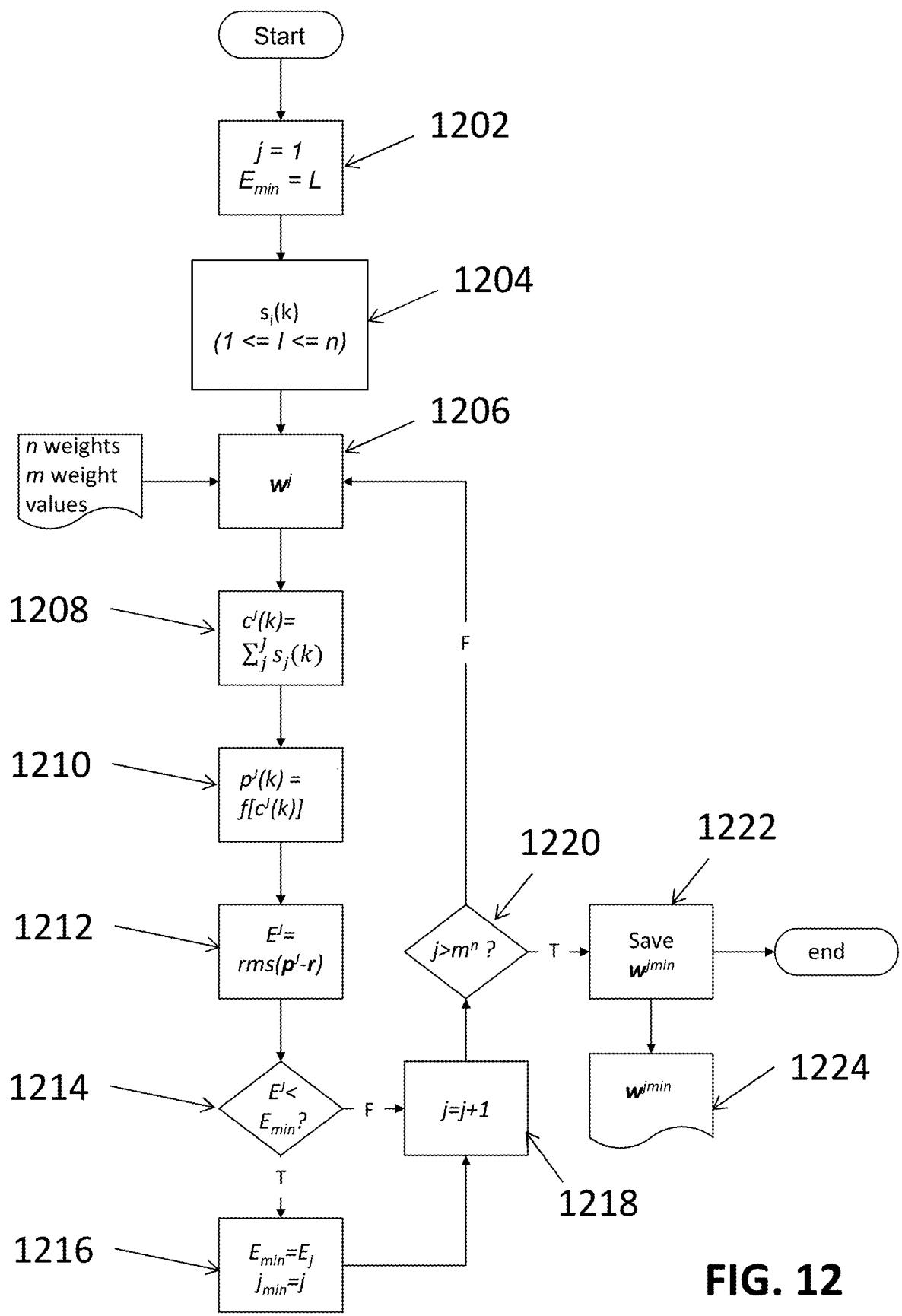
FIG. 12 is a flow chart depicting a method for searching for a preferred set of weights.

FIG. 12 shows a flowchart describing an algorithm used to search for the preferred set of weights. At block 1202, the optimization loop counter j is assigned the value 1 and the minimum error $E_{min}$ is assigned value L, a number chosen to be larger than the error provided by any parameter calculation using any given set of weights. L is a large number, for example, $L=10^{100}$.

At block 1204, a time sequence of n signals is collected using the device hardware. For example, in a device with n=8 light emitters the photo-detector generates a photocurrent that is converted into a voltage signal by a transimpedance amplifier and the voltage signal is converted by an analog-to-digital converter (ADC) into signals $s_i(k)$, representing the signal from LED i at time step k. Using vector notation, in which boldface represents a vector, we have input vector s(k).

At block 1206, a set of weights $w^j$ is selected from a set of m possible weight values, wherein $w^j=[w_1^j \ w_2^j \ \ldots \ w_i^j \ \ldots \ w_n^j]^T$, the superscript T denotes a vector transpose, the superscript j denotes the jth set of weights and the set of possible weight values can be, for example, the set $A\epsilon\{-1, 0,1\}$. That is $w_i^j \epsilon A$ and there are $n^m$ possible combinations for $w^j$ as provided by block 1205, where m is the number of elements in A. At block 1208, the combined signal $c^j(k)$ is calculated by performing a dot product between the weight vector $w^j$ and the input signal vector s(k). At block 1210, the combined signal is used to calculate a parameter of interest, p(k), given by a function f(.) of $c^j(k)$.

At block 1212, an error signal $E_j$ is calculated using, for example, the RMS different between the calculated parameter and a time series signal r(k) obtained from a reference (for example, the EKG signal for heart rate). $E_j$, at block 1214, is compared to the last recorded lowest error, $E_{min}$. If it is smaller than $E_{min}$, its value is recorded, at block 1216, as the new value for $E_{min}$ and j is recorded as the new value of $j_{min}$, the index corresponding to the lowest set of weights. At block 1218, j is incremented and, at block 1220, if j is smaller than or equal to $m^n$ (the highest possible value of j) the weight optimization loop is repeated and the process returns to block 1206. Otherwise, at block 1222, the latest set of preferred weights $w^{jmin}$, provided at block 1224, is saved and the algorithm ends.

Figure 13:
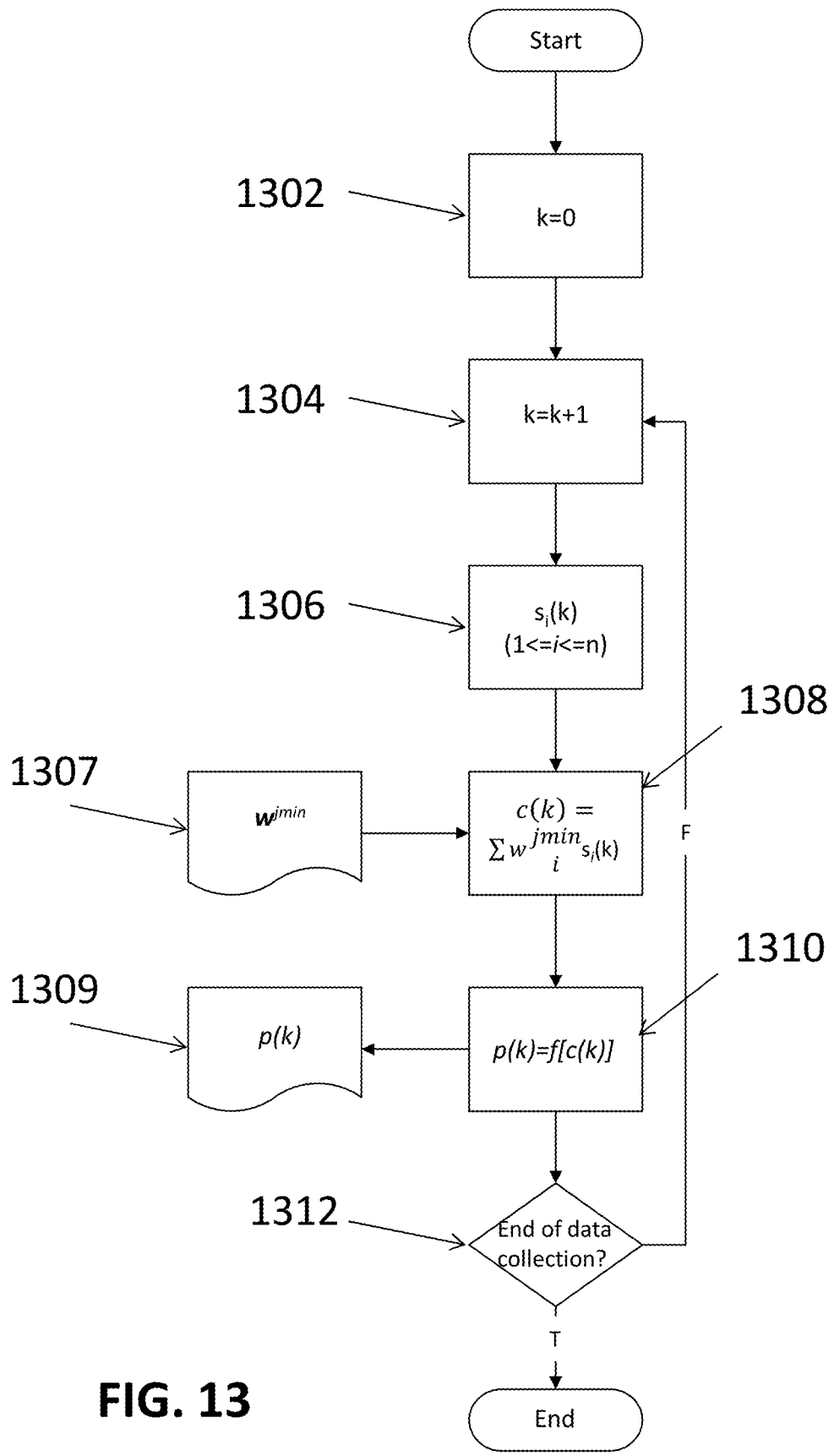
FIG. 13 is a flow chart depicting a method for calculating a parameter of interest using a signal combination technique.

FIG. 13 depicts a flow chart that describes an algorithm used to calculate a parameter of interest, p(k), using the signal combination technique. In this case p(k) is a scalar, for example, a heart rate. The algorithm starts at block 1302, where time step k=0. At block 1304, the time-step loop starts with the time step counter, k, being incremented. At block 1306, new signals $s_i(k)$ are acquired. At block 1308, the combined signal c(k) is calculated by the dot product between s(k) and $w^{jmin}(k)$, provided at block 1307. At block 1310, the parameter of interest, p(k) provided at block 1309, is calculated using the combined signal. The loop repeats itself until the end of data acquisition at block 1312.

Figure 14:
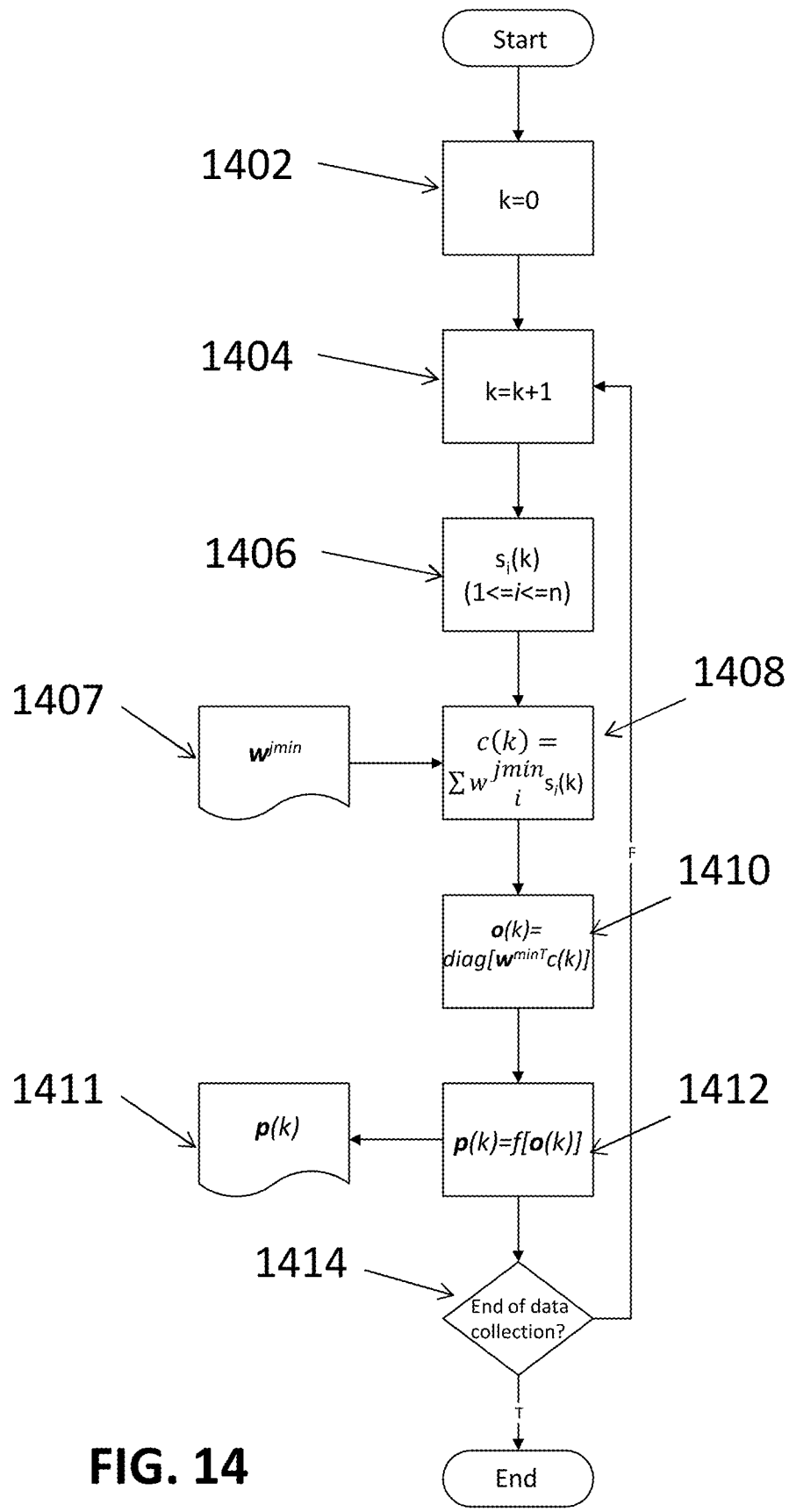
FIG. 14 is a flow chart depicting a method for calculating a parameter of interest when an output parameter is a vector.

The flowchart shown in FIG. 14 describes an algorithm used to calculate a parameter of interest, p(k), in the case when the output parameter is a vector, not a scalar. This is the case, for example, when estimating the quantity of analytes in tissue. For example, oxyhemoglobin, deoxyhemoglobin and water.

The algorithm starts at block 1402 where time step k=0. The time-step loop starts with the time-step counter k, being incremented at block 1404. At block 1406, the new signals $s_i(k)$ are acquired. At block 1408, the combined signal c(k) is calculated by the dot product between s(k) and $w^{jmin}(k)$, provided at block 1407. At block 1410, a vector o(k) is formed by the diagonal elements of the outer product between the combined signal and the preferred weights. This vector is then used as the input to the calculation, at block 1412, of the parameter vector of interest, p(k), wherein p(k), provided at block 1411, can be given, for example, by the matrix multiplication between o(k) and the pseudo-inverse of F, where F is a matrix with rows composed by the absorption coefficients of the analytes of interest at the same peak wavelengths as the illumination sources used to generate the input signal vector s(k). In this case, p(k)=pinv(F)$^T$o(k), where pinv(.) denotes the pseudo-inverse of matrix F. The time-step loop then repeats itself until the end of data collection at block 1414.

Figure 15A:
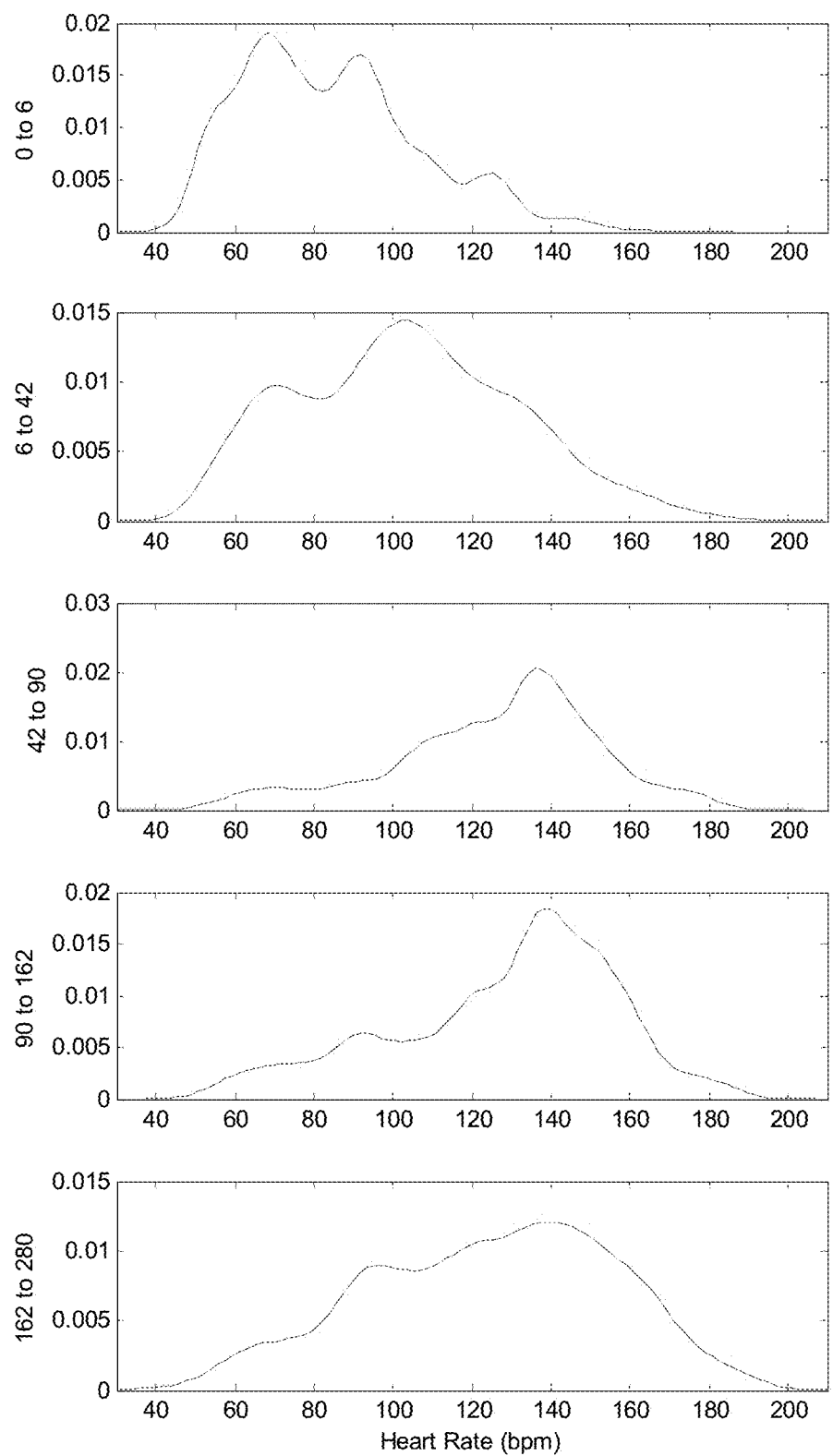
FIG. 15A is a graph showing EKG heart rate distributions for deciles (0-6, 6-42, 42-90, 90-162, and 162-280) of gyroscope total power.
Figure 15B:
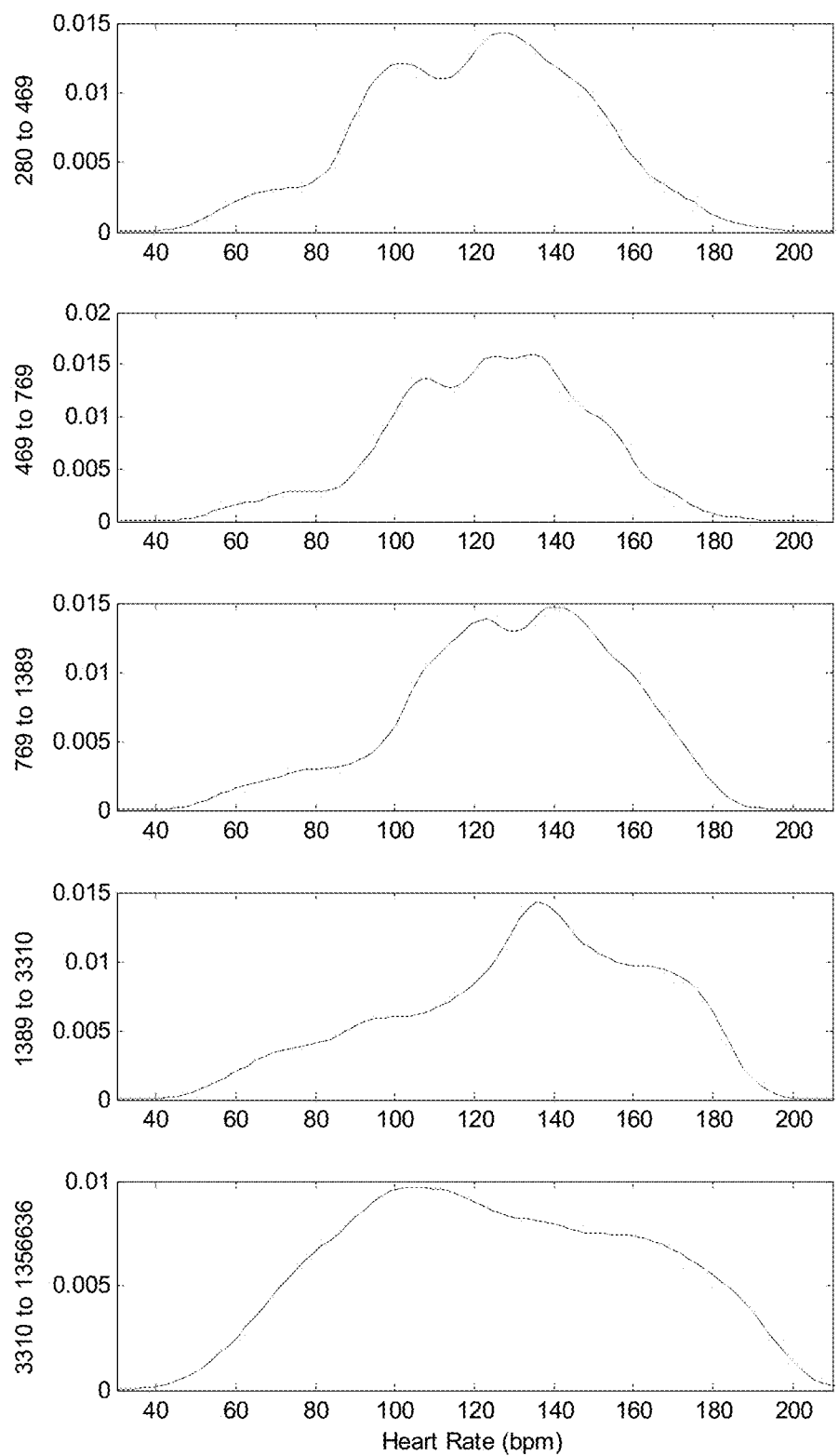
FIG. 15B is a graph showing EKG heart rate distributions for deciles (280-469, 469-769, 769-1389, 1389-3310, and 3310-1356636) of gyroscope total power.

FIG. 15A is a graph showing EKG heart rate distributions for deciles (0-6, 6-42, 42-90, 90-162, and 162-280) of gyroscope total power. FIG. 15B is a graph showing EKG heart rate distributions for deciles (280-469, 469-769, 769-1389, 1389-3310, and 3310-1356636) of gyroscope total power. The graphs illustrated in FIGS. 15A and 15B demonstrate that heart rate distribution is related to device movement.

Figure 16:
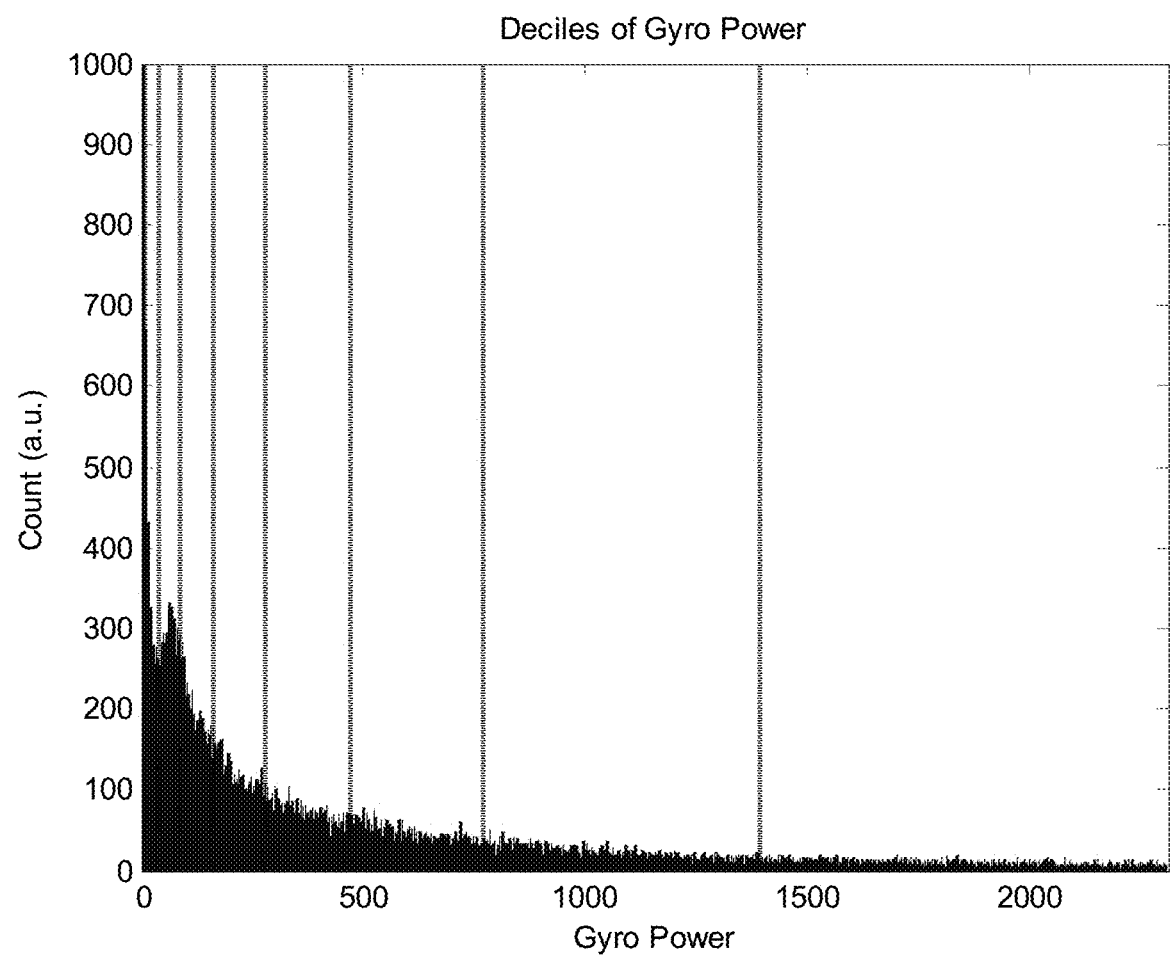
FIG. 16 is a graph showing a histogram of Gyroscope total power signal.

FIG. 16 is a graph showing a histogram of gyroscope total power signal with dashed lines marking deciles of distribution. As illustrated, there is a relationship between the energy present in the gyroscope signal and heart rate distributions, where the signal energy is given by the integral of the modulus squared of the signal. The relationship is clearer at lower heart rates. Noisy spikes happen at most heart rates. This information is implemented in a Bayesian model to eliminate the noise from the gyroscope total power signal to arrive at a heart rate of the user.

The Bayesian estimate of heart rate utilizes two distinct sources of information to develop the best possible estimate of heart rate at any point in time. The Bayesian model propagates a belief distribution through time. The belief is a probability distribution over possible heart rates. It can be discretized so as to only compute belief at relevant heart rates for example 27 bpm to 210 bpm. This range could be reduced for the vast majority of the population. The belief could be initialized uniformly over the range of possible heart rates or based on expected resting heart rates or even on the expected resting heart rate of the user. Once the initial belief is established it is updated in time.

Mathematically, the method can be expressed as $$p(H_t \mid OD_{1:t}) = \eta p(OD_t \mid H_t, M_t) \int p(H_t \mid H_{t-1}, M_t) p(H_{t-1} \mid OD_{1:t-1}) dH_{t-1}$$

$$\text{Belief}(H_t) = \eta p(OD_t \mid H_t, M_t) \int p(H_t \mid H_{t-1}, M_t) \text{Belief}(H_{t+1}) dH_{t-1}$$

$$\text{Belief}(H_t) = \eta p(OD_t \mid H_t, M_t) \sum_{H_{t+1}=\text{Lowest Heart Rate}}^{\text{Highest Heart Rate}} p(H_t \mid H_{t-1}, M_t) \text{Belief}(H_{t-1})$$

wherein OD is the optical density of the optical signal, H is the heart rate, M is the motion signal and η is a normalization constant.

Figure 17:
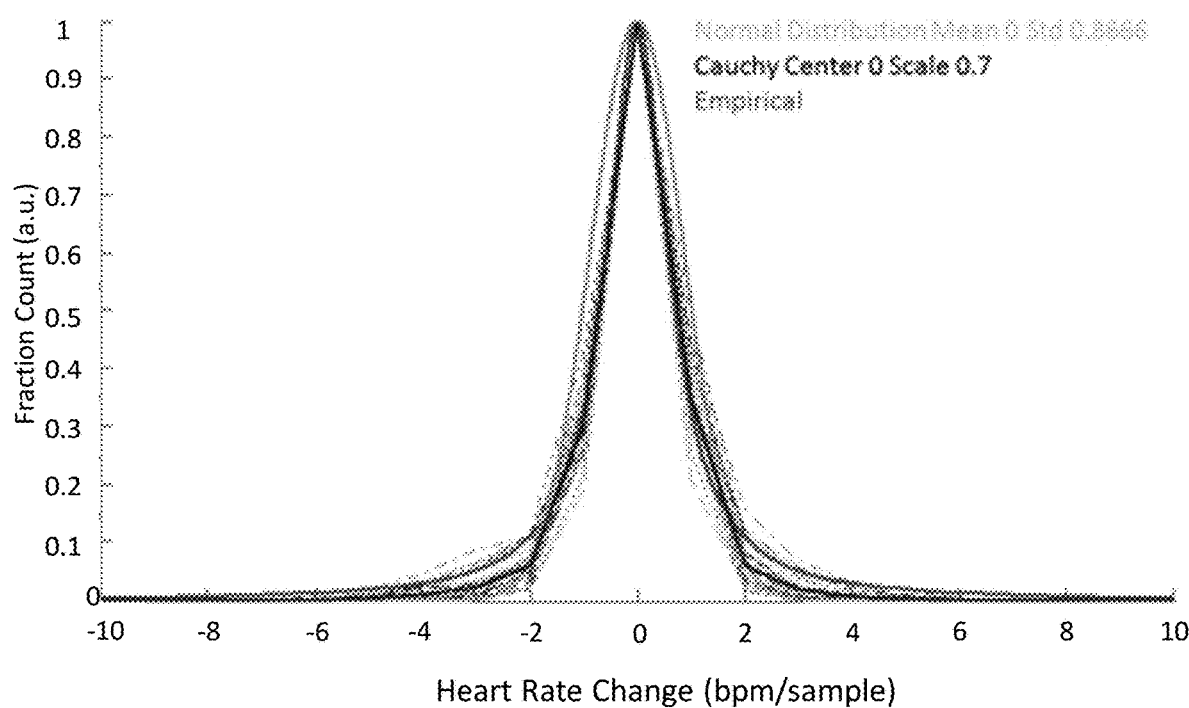
FIG. 17 is a graph showing the distribution of heart rate changes.

The "dynamic model"

$$\sum_{H_{t+1}=\text{Lowest Heart Rate}}^{\text{Highest Heart Rate}} p(H_t \mid H_{t-1}, M_t) \text{Belief}(H_{t+1})$$

updates the belief in the heart rate based on expected changes in heart rate over the short time windows between observations. By examining previous records of heart rates, it can be seen that the change in heart rate over the course of one second is tightly grouped around 0 or no change (FIG. 17). It is expected that if motion is taken into account, the distribution of heart rate changes would be different. For example, if the motion is seen as non-decreasing, the heart rate is non-decreasing and vice versa. The "dynamic model" then takes prior belief in the heart rate distribution and then computes the expected distribution of heart rates. The sum or integral takes into account that the heart rate could move to a given heart rate from a number of previous heart rates.

The "observation model" $p(OD_t|H_t,M_t)$ updates the belief in the heart rate based on the observation of the optical data. There is an assessment as to how likely the optical data would be if it was known what the heart rate and motion were. This could be accomplished in a number of ways. For example, the optical data could be decomposed into frequency distributions and the relative power of each could be compared to determine how likely the observation was. Similarly, a filter bank could be arranged and the power of the resulting signals could be compared to determine the probability of the observation. The frequency content of the motion can be considered. The observational model pODtHt,Mt can be constructed around other input signals indicative of heart rate. For example, pEKGtHt,Mt in which the heart rate input signal is given by an EKG signal. The same Bayesian techniques can be implemented using different input signals, and the dynamic model is likely to remain very similar but could be different depending on the source(s) of the input signal.

The resulting belief is normalized into a true probability at every update. The belief then needs to be reduced to a heart rate to display to the user. This can be accomplished in a number of ways. The expected value of the distribution could be computed and displayed. The heart rate with the highest belief or several other similar schemes could also be used.

The plot in FIG. 17 shows a distribution of heart rate changes (bpm/sample) from 20 subjects undergoing a cycling ramp protocol from rest to exhaustion, including the empirical distribution, a normal fit to the empirical distribution and a Cauchy function fit to distribution, centered at zero with a scale factor of 0.7. The fits are used in the mathematical models to determine the heart rate.

Figure 18:
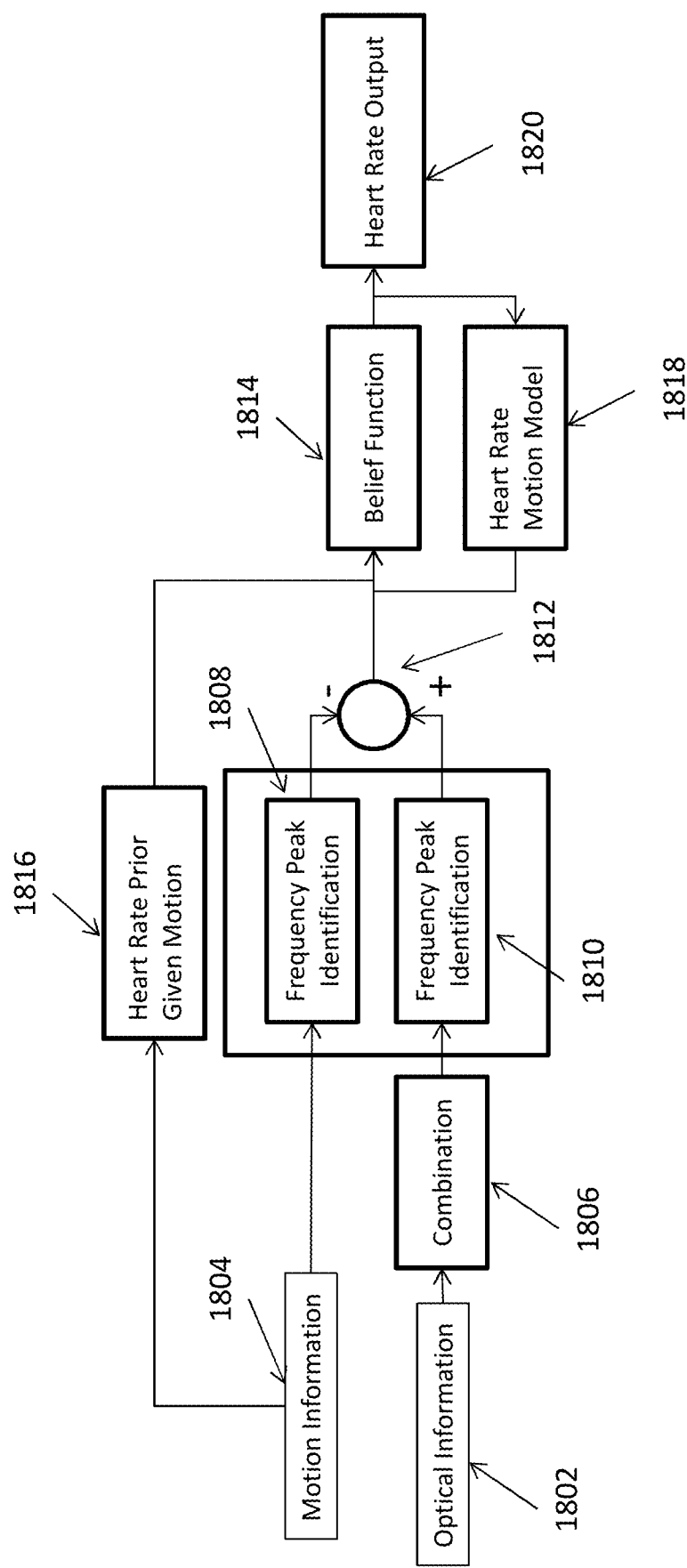
FIG. 18 is a flow chart depicting one example of a method for estimating the heart rate of a user using a Bayesian filter with a motion signal and an optical signal.

The flow chart in FIG. 18 shows one example of a method for estimating the heart rate of a user using a Bayesian filter with a motion signal and an optical signal. In at least one example, the optical signal information at block 1802 and the motion signal information at block 1804 are inputs into the Bayesian filter to estimate the heart rate of the user. The optical signal can include a combination of multiple optical signals at block 1806. The peak frequency of the motion signal at block 1808 and the optical signal, or combined optical signal, at block 1810 is identified. The optical signal can include motion artifacts, so the motion signal can assist in identifying what peaks in the optical signal are real and which are motion artifacts. In at least one example, the identification of the peak frequency of the motion signal can inform the identification of the true peak frequency in the optical signal. In at least one example the optical information at block 1802 and its combination at block 1806 can be represented by additional input signals indicative of the heart rate, including but not limited to an EKG signal, a heart rate component of the separated optical signal, the photoplethysmograph components of the separated optical signal, and their combinations, with or without filtering.

In at least one example, the belief function or future expectation of the heart rate at block 1814 can be adjusted at block 1812 based on the identification of the peak frequencies for the motion signal and the optical signal. Therefore, the future expectation of the heart rate can change based on a change in motion. The future expectation can increase, decrease, or remain constant based on an increase, decrease, or no-change in motion. For example, as motion increases, the expectation of the heart rate increases. The belief function can further inform a heart rate motion model. The belief function, along with the prior heart rate with a given motion at block 1816 and heart rate motion model at block 1818 can be used to update the estimate of the heart rate of the user at block 1820.

What is claimed is:

1. A method for estimating a user's heart rate, the method comprising:
    emitting light to the user from two emitters having at least one wavelength, each of the two emitters located different distances from a photodetector;
    receiving, by the photodetector, at least two reflected light signals from the user;
    receiving, from at least one sensor on an electronic device at a time, at least one input signal based on the at least two reflected light signals, wherein the input signal is a noisy signal indicative of heart rate;
    receiving, from a gyroscope or an accelerometer on an electronic device at the time of receiving the at least one input signal, a motion signal; and
    combining the at least one input signal and the motion signal via application of a Bayesian filter to estimate the heart rate of the user for the time of receiving the at least one input signal and the motion signal,
    wherein in combining the at least one input signal the motion signal, peaks of the motion signal assists in determining which peaks in the input signal are real and which of the peaks in the input signal are motion artifacts.

2. The method of claim 1, further comprising separating the at least one input signal into signal components prior to applying the Bayesian filter.

3. The method of claim 2, wherein separating the input signal is performed using one or more of the following: short-time Fast Fourier Transforms, tone-detection, or mean-absolute difference autocorrelation.

4. The method of claim 2, wherein separating the at least one input signal is performed using an autocorrelation of the at least one input signal.

5. The method of claim 4, wherein at least one peak of the autocorrelation signal is used to detect the heart rate.

6. The method of claim 1, wherein the input signal is an optical signal, a combination of optical signals, or combinations thereof.

7. The method of claim 1, wherein the method further comprises:
    combining the at least two reflected light signals to form the input signal.

8. The method of claim 7, wherein the at least two reflected light signals are from the same emitted wavelength separated by a period of time.

9. The method of claim 7, wherein the at least two reflected light signals are from at least two emitters emitting at least two different wavelengths.

10. The method of claim 7, wherein the combination is a linear combination.

11. The method of claim 7, wherein at least three different wavelengths of light are detected.

12. The method of claim 11, wherein the at least three different wavelengths are 550 nm, 650 nm, and 950 nm.

13. The method of claim 11, wherein the at least three different wavelengths are 505 nm, 470 nm, and 630 nm.

14. The method of claim 1, wherein the emitted wavelengths are within a range of about 450 nm to about 1100 nm.

15. The method of claim 1, further comprising repeating the steps of claim 1 after a period of time and updating the estimate of the user's heart rate.

16. The method of claim 15, further comprising determining an expected change in the heart rate using the motion signal.

17. The method of claim 16, wherein the estimated heart rate is updated based on the expected change in heart rate.

18. The method of claim 16, wherein the expected change in heart rate is increasing, decreasing, or unchanging.

19. A device for tissue monitoring of a user, comprising:
two emitters configured to emit at least one wavelength of light;
a photodetector configured to receive at least two reflected light signals at a time, each of the two emitters located a different distance from the photodetector;
a gyroscope or an accelerometer configured to detect a motion signal of the user; and
a processing component coupled with the photodetector and the gyroscope or the accelerometer, the processing component configured to:
calculate a combination of the at least two reflected light signals;
receive, from the gyroscope or the accelerometer at the time of receiving the at least one input signal, the motion signal; and
combining the at least one input signal and the motion signal via application of a Bayesian filter to estimate a heart rate of the user for the time of receiving the at least one input signal and the motion signal,
wherein in combining the at least one input signal the motion signal, peaks of the motion signal assists in determining which peaks in the input signal are real and which of the peaks in the input signal are motion artifacts.

* * * * *